United States Patent [19]
Hase

[11] Patent Number: 6,033,459
[45] Date of Patent: Mar. 7, 2000

[54] GAS COLLECTION APPARATUS, GAS ANALYZING APPARATUS USING THE SAME AND GAS ANALYZING METHOD

[75] Inventor: Ushio Hase, Tokyo, Japan

[73] Assignee: NEC Corporation, Tokyo, Japan

[21] Appl. No.: 09/114,291

[22] Filed: Jul. 13, 1998

[30] Foreign Application Priority Data

Jul. 15, 1997 [JP] Japan ................................. 9-189831

[51] Int. Cl.$^7$ .................................................. B01D 15/08
[52] U.S. Cl. ........................... 95/82; 73/23.39; 73/31.02; 73/61.52; 96/104; 210/656; 210/198.2
[58] Field of Search ............................... 55/524; 73/23.2, 73/23.39, 23.4, 31.02, 61.52, 61.53; 95/82, 86, 89; 96/101, 104; 210/656, 198.2

[56] References Cited

U.S. PATENT DOCUMENTS

| | | |
|---|---|---|
| 4,138,336 | 2/1979 | Mendel et al. ......................... 210/198.2 |
| 4,917,709 | 4/1990 | Hall et al. .................................. 95/82 |
| 5,128,291 | 7/1992 | Wax et al. ......................... 210/198.2 X |
| 5,458,783 | 10/1995 | Levy et al. ......................... 210/198.2 X |
| 5,567,307 | 10/1996 | Karmarkar ........................... 210/198.2 |
| 5,651,886 | 7/1997 | Hoffmann et al. .................... 96/101 X |

FOREIGN PATENT DOCUMENTS

| | | |
|---|---|---|
| 1-41857 | 2/1989 | Japan . |
| 08015250 | 1/1996 | Japan . |
| 08054380 | 2/1996 | Japan . |
| 08094502 | 4/1996 | Japan . |
| 08099041 | 4/1996 | Japan . |
| 08101102 | 4/1996 | Japan . |
| 08196903 | 8/1996 | Japan . |
| 08233706 | 9/1996 | Japan . |
| 09083005 | 3/1997 | Japan . |

OTHER PUBLICATIONS by P.F. Lindgren et al., "Measurement of Atmospheric Sulfur Dioxide by Diffusion Scrubber Coupled Ion Chromatograpy", *American Chemical Society*, 1988, pp. 19–24.

by P.K. Simon et al., "Wet Effluent Denuder Coupled Liquid/Ion Chromatography", *American Chemical Society*, 1991, pp. 1237–1242.

Primary Examiner—Robert Spitzer
Attorney, Agent, or Firm—Young & Thompson

[57] ABSTRACT

In a denuder (2) serving as a gas collection apparatus, an absorption liquid supply tube (4) for spraying absorption liquid from a nozzle (4a) to the inner wall of a denuder pipe (2a) is provided at the upper portion of the denuder pipe (2a). A sample atmospheric air supply tube (7) for supplying sample atmospheric air into the denuder (2) is provided at the lower portion of the denuder pipe (2a). On the inner wall of the denuder pipe (2a) is formed a photocatalyst thin film layer (13) containing photocatalyst which is optically excited to be made super-hydrophilic upon irradiation of light having specific wavelengths (for example, ultraviolet rays) thereto.

16 Claims, 11 Drawing Sheets

F I G. 4
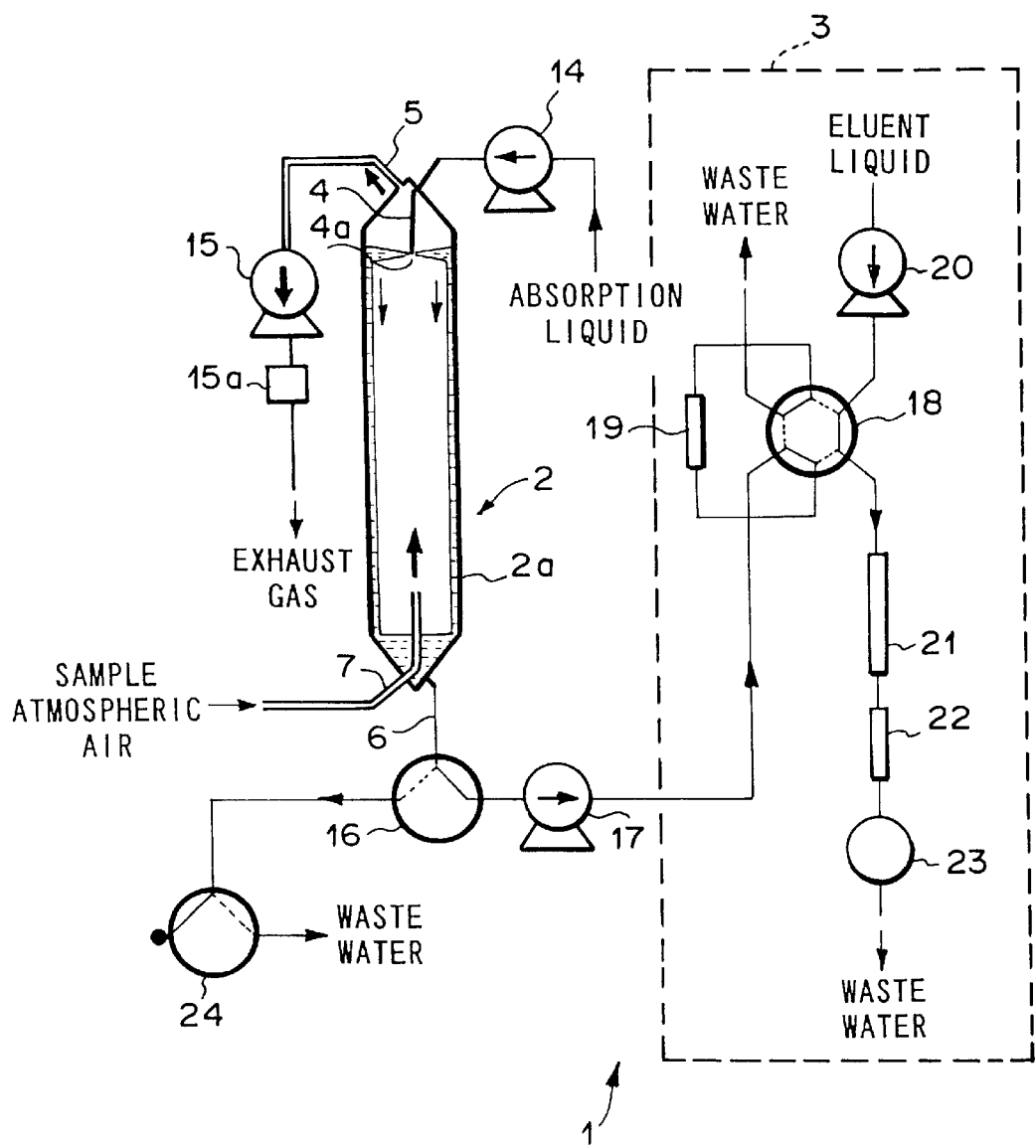

F I G . 12
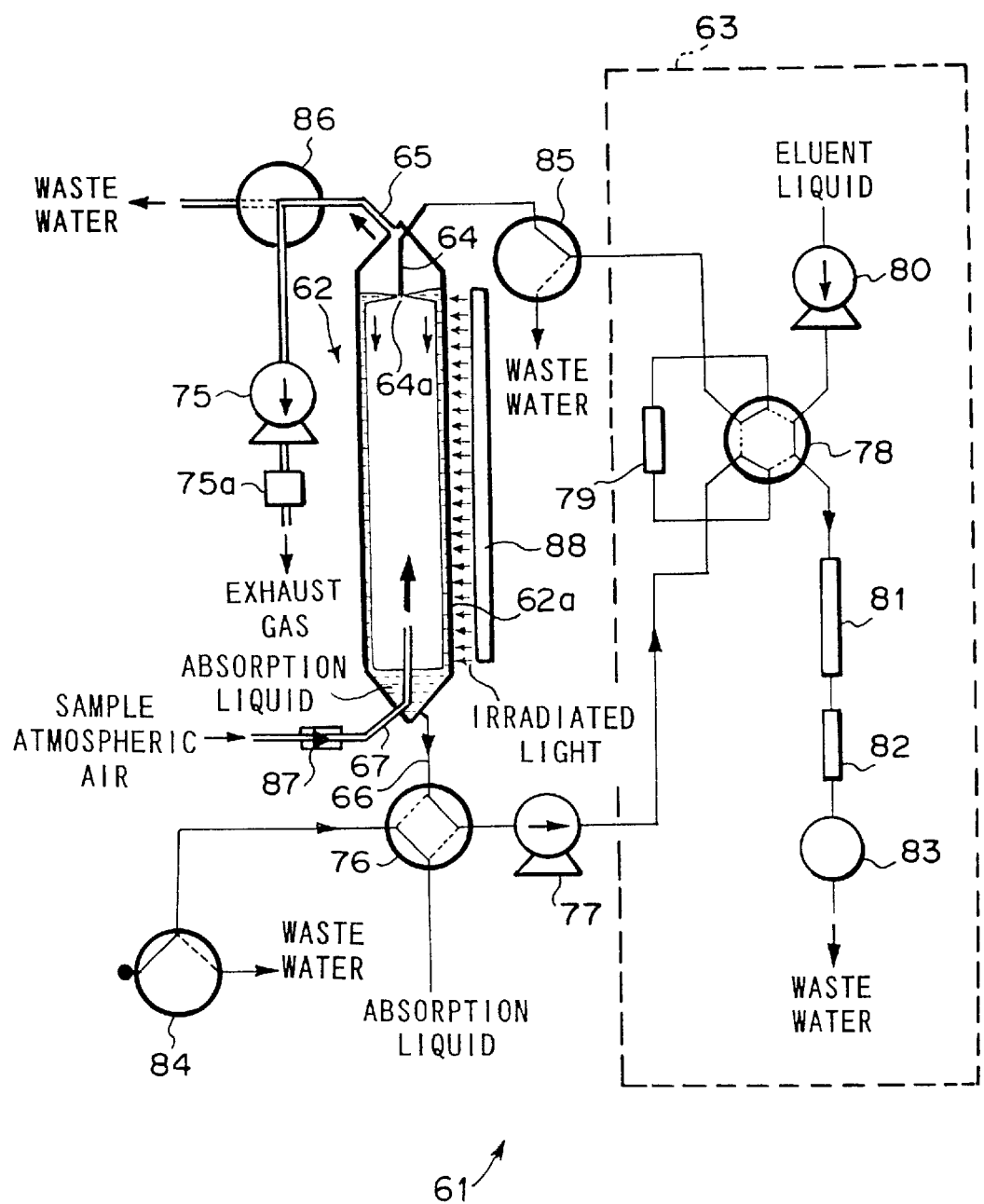

6,033,459

GAS COLLECTION APPARATUS, GAS ANALYZING APPARATUS USING THE SAME AND GAS ANALYZING METHOD

BACKGROUND OF THE INVENTION

1. Field of the Invention

The present invention relates to a gas collecting apparatus for collecting a trace quantity of gas components or volatile components in atmospheric air to continuously monitor the gas components or volatile components, a gas analyzing system using the gas collecting apparatus, and a gas analyzing method.

2. Description of the Related Art

The following two methods have been hitherto utilized as a method of analyzing gas components in atmospheric air. According to one method, an analysis operator collects samples in the field and carries them back to an analysis room to make analyses on the samples with various analysis methods. According to the other method, with respect to special components, an analysis apparatus comprising a sensor and a recording device is deployed in the field to monitor these special components. The sample collection work (sampling work) in the field is frequently performed by causing analysis components (samples) to be absorbed by absorption liquid or absorbent. When the absorption liquid is used, the analysis of the components is performed by using the absorption liquid itself. On the other hand, when the absorbent is used, the analysis of the components is performed by using extraction liquid (eluate) which has obtained by adding eluent to the absorbent to elute the components.

Liquid chromatography such as a high-speed liquid chromatography, ion chromatography or the like has merit in that many components in liquid can be analyzed with high sensitivity by using only one sample. Particularly, the ion chromatography used to analyze inorganic components can more easily analyze anion components for which an analysis operation becomes more cumbersome using other analysis methods, and this causes ion chromatography to be widely utilized. Even in the case of analysis of acidic gas components in the atmospheric air, the method of carrying the samples back to an analysis room and then analyzing absorption liquid or extraction liquid with the ion chromatography is mainly used as described above.

According to a widely used method based on use of absorption liquid, a predetermined amount of absorption liquid is fed into a bubbler or an impinger and the atmospheric air is sucked into the bubbler or the impinger and then bubbling or impinging is carried out to solve an analysis target component into absorption liquid. At present, an automatic monitor using this method has been developed, and the monitoring on the ground can be carried out.

Another easily automated method which has been developed incorporates a sample collection method using a gas permeable membrane (so-called diffusion scrubber method) as disclosed in "Analytical Chemistry", Vol. 61, No. 1 (January 1989), pp19–24, Japanese Patent Application Laid-open No. Hei-8-54380.

FIG. 1 is a diagram showing the construction of a diffusion scrubber body in a conventional gas analysis apparatus. As shown in FIG. 1, a diffusion scrubber body 101 has an inner pipe 102 of a gas permeable membrane tube and an outer pipe 103 into which the inner pipe 102 is inserted.

In the diffusion scrubber body 101, analysis components in a sample of atmospheric air are absorbed by absorption liquid while the sample atmospheric air is passed into the inner pipe 102 and the absorption liquid is passed through the gap between the inner pipe 102 and the outer pipe 103.

In a special case, the diffusion scrubber method can collect analysis target components such as hydrochloric acid, nitric acid, ammonia, etc. with a high collection rate of 90% or more, however, in general cases, the collection rate is not so high. In addition, fine particles in the sample atmospheric air are adsorbed onto the surface of the gas permeable membrane, resulting in variation of the collection rate overtime. Accordingly, this method is suitably applied to analysis which is limited to a component such as ammonia or the like for which the collection rate is high, and carried out in a clean room where the amount of fine particles is very low. However, this method is not necessarily suitable for a case where the sample atmospheric air is normal outside air or indoor air and a case where impurity components in the sample atmospheric air are required to be qualitatively grasped. This problem occurs because the sample atmospheric air and the absorption liquid are not brought into direct contact with each other.

As means of solving this problem, a wet denuder method has been developed, and it is disclosed in "Analytical Chemistry", Vol. 63, No. 13, July 1991. A conventional gas analysis apparatus using the wet denuder method will be described hereunder with reference to FIGS. 2 and 3.

FIG. 2 is a diagram showing the overall construction of a conventional gas analysis apparatus using the wet denuder method, and FIG. 3 is an enlarged cross-sectional view showing the main body of the denuder.

In the conventional gas analysis apparatus 201 using the wet denuder method, absorption liquid is passed from the upper side to the lower side along the inner wall of a denuder 202 serving as a gas collection apparatus as shown in FIG. 2, and also sample atmospheric air is passed from the lower side to the upper side in the denuder 202 by actuating a suction pump 203. The flow rate of the sample atmospheric air flow caused by the suction pump 203 is adjusted by a flow-rate controller 217.

In the denuder 202, a silica gel coat glass pipe 204 obtained by growing a silica gel film on the inner wall of a glass pipe (hereinafter referred to as "glass pipe 204") is provided, on the upper portion thereof, with an absorption liquid supply tube 205 for supplying absorption liquid into the glass pipe 204, and a sample atmospheric air exhaust pipe 206 for exhausting the sample atmospheric air from the glass pipe 204. Further, the glass pipe 204 is also provided, on the lower portion thereof, with an absorption liquid exhausting tube 207 for exhausting the absorption liquid from the glass pipe 204, and a sample atmospheric air supply pipe 208 for supplying the sample atmospheric air into the glass pipe 204.

The absorption liquid supplied from the absorption liquid supply tube 205 into the glass pipe 204 is passed through a filter 206'; and then downwardly flows along the inner wall of the glass pipe 204. On the other hand, the sample atmospheric air supplied from the sample atmospheric air supply tube 208 is passed through the glass pipe 204, and then exhausted from the sample atmospheric air exhaust pipe 206. At this time, the absorption liquid and the sample atmospheric air come into direct contact with each other, so that analysis components in the sample atmospheric air are absorbed into the absorption liquid. The absorption liquid which has absorbed the analysis components are exhausted from the absorption liquid exhaust pipe 207 to the outside of the glass pipe 204.

The absorption liquid exhausted from the absorption liquid exhaust tube 207 is fed to an ion chromatograph 210 by a liquid feeding pump 209 shown in FIG. 2. As shown in FIG. 2, the ion chromatograph 210 includes flow path switching valves 211a and 211b for switching a flow path for the absorption liquid, sample loops 212a, 212b for temporarily stocking the absorption liquid, a separation column 213 for separating analysis components from the absorption liquid to make analyses on the components, a suppressor 214 and a conductivity detector 215.

The flow path of the absorption liquid fed to the ion chromatograph 210 is switched by the flow path switching valve 211a to temporarily stock the absorption liquid in the sample loop 212a or the sample loop 212b. Thereafter, by switching to the flow path switching valve 211b, the absorption liquid which is stocked in the sample loop 212a or the sample loop 212b flows through the separation column 213, the suppressor 214 and the conductivity detector 215 in this order by the liquid feeding pump 216, whereby the analysis components are separated from the absorption liquid. The analysis components thus separated are analyzed and the concentration of the analysis components in the sample atmospheric air is calculated on the basis of the analysis result.

According to the conventional gas analysis apparatus 201 thus constructed, the collection rate of the analysis components is dependent on the contact area of the absorption liquid and the sample atmospheric air, and precision of concentration measurement of the analysis components is dependent on the reproducibility of the contact area of the absorption liquid and the sample atmospheric air on the surface of the inner wall of the glass pipe 204. Therefore, in the conventional analysis apparatus 201, a silica gel film is formed on the surface of the inner wall of the glass pipe 204 to enhance the wettability of the absorption liquid on the surface of the inner wall of the glass pipe 204, and also to make the absorption liquid uniform. In addition, the absorption liquid supplied from the absorption liquid supply tube 205 is passed through the filter 206', whereby the absorption liquid is dispersed onto the overall surface of the inner wall of the glass pipe 204.

However, the conventional gas analysis apparatus has the following disadvantage. That is, when it is used for a long period organic components in the atmospheric air are adsorbed onto the surface of the silica gel film of the silica gel coat glass pipe serving as the gas collection apparatus. As a result, the wettability of the surface of the inner wall of the glass pipe is reduced where the organic components are adsorbed. Therefore, the wettability of the absorption liquid on the surface of the inner wall of the glass pipe is non-uniform, the collection rate of the analysis components is varied over time, and the measurement precision of the concentration of the analysis components is reduced.

In order to prevent the time variation of the collection rate, etc., it is necessary to clean the inner wall of the silica gel coat glass pipe with detergent or alcohol, and thus maintenance and cleaning must be periodically performed. This causes a burden on a user of the gas analysis apparatus.

BRIEF SUMMARY OF THE INVENTION

Therefore, an object of the present invention is to provide a gas collection apparatus in which the collection rate of analysis components is not lowered, even when the apparatus, a gas analysis apparatus using the gas collection apparatus, and a gas analyzing method using the gas collection apparatus, is used for a long period, and maintenance and cleaning works are not required to be periodically carried out.

Here, related techniques will be first described as a reference to prevent adhesion of organic components or the like in sample atmospheric air to the inside of the gas collection apparatus.

First, Japanese Laid-open Patent Application Laid-open No. Hei-9-83005 discloses a technique for coating the surface of a solar cell with a transparent layer containing a photocatalyst. This technique relates to a protection cover for a solar battery. When the surface of the protection cover of a solar cell is covered by a photocatalyst layer, the photocatalyst layer is optically excited by solar light and the surface of the photocatalyst layer becomes super-hydrophilic to the extent that the contact angle with water is equal to about zero degrees. When the solar cell is exposed to rain, soil adhering to the surface of the protection cover is washed by the rain water, whereby the surface of the protection cover is self-cleaned.

Further, Japanese Laid-open Patent Application No. Hei-8-99041 discloses that when titanium oxide in anatase crystalline form, which is one of the representative photocatalysts, is formed on the surface of the substrate so that it is transparent and porous, the titanium oxide adsorbs atmosphere polluting materials, and the atmosphere polluting materials can be quickly, effectively and continuously decomposed and removed by irradiating light thereto.

Still further, Japanese Laid-open patent application Laid-open No. Hei-8-94502, etc. discloses that NO and $NO_2$ are chemically changed to water-soluble materials upon action of a photocatalyst such as titanium oxide or the like.

The present invention has been implemented by applying the characteristics of the photocatalysts as described above.

In order to attain the above object, according to a first aspect of the present invention, a gas collection apparatus having a pipe in which sample atmospheric air serving as a measurement target is supplied and passed, and absorption liquid adapted to absorb analysis components contained in the sample atmospheric air is supplied and passed along the inner wall of the pipe. The inner wall is characterized by having a photocatalyst thin film layer containing a photocatalyst which is optically excited upon being irradiated by light having specific wavelengths. When irradiated, the thin film layer is made super-hydrophilic, and the pipe is formed of material which allows the light having specific wavelengths to be transmitted therethrough.

According to the gas collection apparatus described above, when the light having the specific wavelengths for optically exciting the photocatalyst irradiates to the gas collection apparatus, the surface of the photocatalyst thin film layer is made super-hydrophilic to the extent that the contact angle with water is equal to about zero degrees. Therefore, organic materials, etc. which adhere to the surface of the photocatalyst thin film layer are easily washed out by the absorption liquid, and the surface of the photocatalyst thin film layer is self-cleaned.

It is preferable that the light having the specific wavelengths be ultraviolet rays which are contained in light emitted from a white light source or solar light, and that the photocatalyst be formed of a material from which the same components as the analysis components, or components interfering with the analysis of the analysis components are eluted into the absorption liquid at such a small amount that the elution of these components has no effect on the analysis precision of the analysis components.

The photocatalyst is preferably formed of anatase type titanium oxide or rutile type titanium oxide.

The photocatalyst thin film layer is preferably designed to be transparent and to have a thickness of 0.01 $\mu$m to 5 $\mu$m.

The photocatalyst thin film layer is preferably designed to be porous, thereby enhancing an efficient photochemical reaction between the photocatalyst and organic materials, etc. which adhere to the surface of the photocatalyst thin film layer.

The pipe is preferably designed so that the light attenuation coefficient of the pipe wall at the specific wavelengths is equal to 90% or less, and more preferably 50% or less.

In addition, the apparatus is preferably provided with a cooling apparatus for cooling a part or the overall of the inside of the pipe, thereby suppressing vaporization of the absorption liquid, and thus preventing reduction of the collection rate of analysis components in the sample atmospheric air.

The cooling temperature of a part or the overall of the inside of the pipe by the cooling apparatus is preferably set to 0° C. to 10° C.

Further, according to a second aspect of the present invention, a gas analysis apparatus according to the present invention includes the above-described gas collection apparatus, and a component detection apparatus to which the absorption liquid is fed along the inner wall of the pipe to detect analysis components contained in the absorption liquid, wherein the gas collection apparatus is disposed under an environment which is exposed to the light having specific wavelengths which is adapted to optically excite the photocatalyst of the photocatalyst thin film layer formed on the inner wall of the pipe, and is irradiated from a white light source or the sun. Accordingly, the photocatalyst of the photocatalyst thin film layer which is formed on the pipe of the gas collection apparatus is optically excited by the light at all times to make the surface of the photocatalyst thin film layer super-hydrophilic. Therefore, the organic materials, etc. which adhere to the surface of the photocatalyst thin film layer are immediately washed out by the absorption liquid.

Further, the component detection apparatus comprises concentrating means for concentrating analysis components contained in the absorption liquid, desorption means for desorbing from the concentrating means the analysis components concentrated by the concentrating means, and component detection means for detecting the analysis components which are desorbed from the concentrating means. Therefore, the analysis components are detected while concentrated, so that the detection intensity of the analysis components can be enhanced, resulting in enhancement of the analysis precision.

The concentrating means of the component detection apparatus preferably comprises a concentrating column which is filled with adsorbent for adsorbing the analysis components contained in the absorption liquid.

The absorption liquid from which the analysis components are removed when it is passed through the concentrating means is circulatively fed to the gas collection apparatus, whereby the amount of the absorption liquid itself which is used for measurements is set to be fixed irrespective of the flow rate of the absorption liquid. Therefore, the flow rate of the absorption liquid can be set to any value within such a range that no capturing loss of the analysis components occurs in the concentrating means.

The component detection apparatus preferably comprises a liquid chromatograph or an ion chromatograph.

Further, the apparatus is provided with an exciting light source for continuously or intermittently irradiating to the pipe the light having the specific wavelengths to optically excite the photocatalyst contained in the photocatalyst thin film layer formed on the inner wall of the pipe of the gas collection apparatus. In this case, the activity of the photocatalyst thin film layer is greatly enhanced, and components such as NO, $NO_2$, etc. which have low solubility in the absorption liquid without being modified, are oxidized into nitrous acid, etc. which are soluble in the absorption liquid.

According to a third aspect of the present invention, a gas analysis method using the above-described gas analysis apparatus comprising a first component analyzing step of collecting the analysis components serving as analysis targets from the sample atmospheric air serving as a measurement target by the gas collection apparatus in a state where the exciting light source is turned off, and then analyzing the analysis components thus collected by the component detection apparatus, and a second component analysis step of collecting the analysis components serving as analysis targets from the sample atmospheric air serving as a measurement target by the gas collecting apparatus in a state where the exciting light source is turned on, and then analyzing the analysis components thus collected by the component detection apparatus.

According to the gas analysis method, when the analysis components are collected under the state that the exciting light source is turned off, the photocatalyst thin film layer is activated to the extent that the surface of the inner wall of the pipe is prevented from being soiled, and only water-soluble analysis components in the sample atmospheric air are collected by the absorption liquid. On the other hand, when the analysis components are collected under the state that the exciting light source is turned on, the photocatalyst thin film layer is greatly activated to the extent that analysis components such as NO, $NO_2$, etc. which are little soluble in the absorption liquid with no modification are oxidized into nitrous acid, etc. which are soluble in the absorption liquid.

BRIEF DESCRIPTION OF THE DRAWINGS

FIG. 4 is a diagram showing the construction of a first mode of a gas analysis apparatus of the present invention;

FIG. 12 is a diagram showing the construction of a third mode of the gas analysis apparatus of the present invention.

DETAILED DESCRIPTION OF THE INVENTION

Preferred embodiments of the present invention will be described hereunder with reference to the accompanying drawings.

FIG. 4 is a diagram showing the construction of a gas analysis apparatus according to the present invention.

As shown in FIG. 4, the gas analysis apparatus 1 has a denuder 2 serving as a gas collection apparatus for collecting analysis components to be analyzed from sample atmospheric air, and an ion chromatograph 3 serving as a component detection apparatus for detecting the analysis components collected by the denuder 2.

Figure 5:
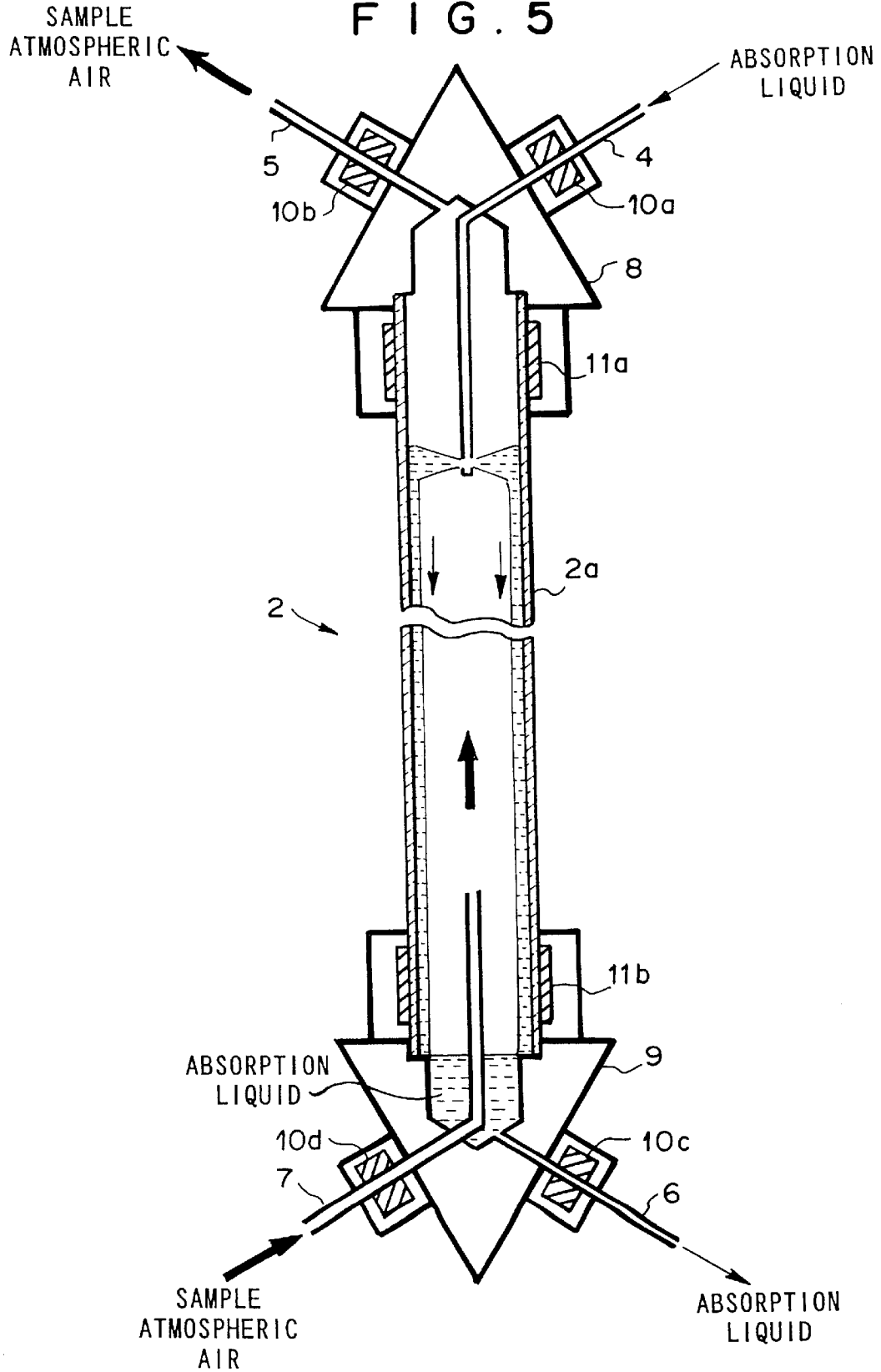
FIG. 5 is a cross-sectional view showing the detailed construction of the denuder shown in FIG. 4.

First, the denuder 2 will be briefly described with reference to FIGS. 4 and 5. FIG. 5 is a cross-sectional view showing the detailed construction of the denuder shown in FIG. 4.

As shown in FIGS. 4 and 5, the denuder 2 is provided, at the upper portion thereof, with an absorption liquid supply tube (pipe) 4 for supplying absorption liquid into a denuder pipe 2a, and a sample atmospheric air exhaust tube (pipe) 5 for exhausting the sample atmospheric air from the inside of the denuder pipe 2a. Further, the denuder 2 is also provided, at the lower portion thereof, with an absorption liquid exhaust tube (pipe) 6 for exhausting the absorption liquid from the inside of the denuder pipe 2a, and a sample atmospheric air supply tube (pipe) 7 for supplying the sample atmospheric air into the inside of the denuder pipe 2a.

As shown in FIG. 5, the absorption liquid supply tube 4 and the sample atmospheric air exhaust tube 5 are provided at the upper portion of the denuder pipe 2a through a connection joint 8, and the absorption liquid exhaust tube 6 and the sample atmospheric air supply tube 7 are provided at the lower portion of the denuder pipe 2a through a connection joint 9. Seal members 10a, 10b, 10c, 10d are disposed at the connection portion between the absorption liquid supply tube 4 and the connection joint 8, at the connection portion between the sample atmospheric exhaust tube 5 and the connection joint 8, at the connection portion between the absorption liquid exhaust tube 6 and the connection joint 9 and at the connection portion between the sample atmospheric air supply tube 7 and the connection joint 9, respectively. In addition, seal members 11a and 11b are disposed at the connection portion between the connection joint 8 and the denuder pipe 2a and at the connection portion between the connection joint 9 and the denuder pipe 2a, respectively. Accordingly, this sealing application prevents contamination of the external gas and leakage of the absorption liquid.

In the denuder 2 thus constructed, when the absorption liquid is fed into the absorption liquid supply tube 4 by a first liquid feeding pump 14, the absorption liquid is sprayed from a nozzle 4a provided at the tip of the absorption liquid supply tube 4 toward the inner wall of the denuder pipe 2a, and flows down along the inner wall of the denuder pipe 2a. Further, by actuating a suction pump 15, the sample atmospheric air is supplied from the sample atmospheric supply tube 7 into the denuder pipe 2a, passed through the denuder 2 and then finally exhausted from the sample atmospheric air exhaust tube 5. At this time, the absorption liquid and the sample atmospheric air are brought into direct contact with each other, so that the analysis components in the sample atmospheric air are absorbed into the absorption liquid. The absorption liquid which has absorbed the analysis components is exhausted from the absorption liquid exhaust tube 6 to the outside of the denuder pipe 2a.

The absorption liquid exhausted from the absorption liquid exhaust tube 6 is fed through a first flow-path switching valve 16 to a second liquid feeding pump 17, and then fed to the ion chromatograph 3.

The flow rate of the absorption liquid in each of the liquid feeding pumps 14 and 17 is set to a predetermined value by a flow-rate adjusting mechanism (not shown) which is provided to each liquid feeding pump, and the flow rate of the suction pump 15 is set to a predetermined value by a flow-rate controller 15a.

Next, the ion chromatograph 3 will be briefly described.

As shown in FIG. 4, the ion chromatograph 3 includes a third flow-path switching valve 18 for switching the flow path of the absorption liquid fed, a concentrating column 19 serving as concentrating means for adsorbing the analysis components collected in the absorption liquid, a third liquid feeding pump 20 for feeding eluent liquid for eluting the analysis components adsorbed in the concentrating column 19, and, a separation column 21, a suppressor 22 and a conductivity detector 23 which serve as detection means for separating the analysis components from each other to detect each of the analysis components. The eluent liquid functions as desorption means for releasing the analysis components from the concentrating column 19 serving as the concentrating means.

The absorption liquid which is fed to the ion chromatograph 3 is fed to the concentrating column 19 through the third flow-path switching valve 18. In the concentrating column 19, the analysis components contained in the absorption liquid are captured to be concentrated, and the residual absorption liquid is wasted through the third flow-path switching valve 18. Subsequently, by switching the third flow-path switching valve 18 to a flow path indicated by a broken line and actuating the third liquid feeding pump 20, the eluent liquid is fed through the third flow-path switching valve 18 to the concentrating column 19, and the analysis components concentrated by the concentrating column 19 are eluted into the eluent liquid. The flow rate of the liquid in the third liquid feeding pump 20 is set to a predetermined value by a flow-rate adjusting mechanism (not shown).

The eluent liquid (eluate) containing the analysis components is passed through the third flow-path switching valve 18 and then flows into the separation column 21, the suppressor 22 and the conductivity detector 23 in this order, whereby the analysis components are separated from each other in the separation column 21 and analyzed by the detector 23. The concentration of the analysis components in the sample atmospheric air is determined on the basis of the analysis result.

Figure 6:
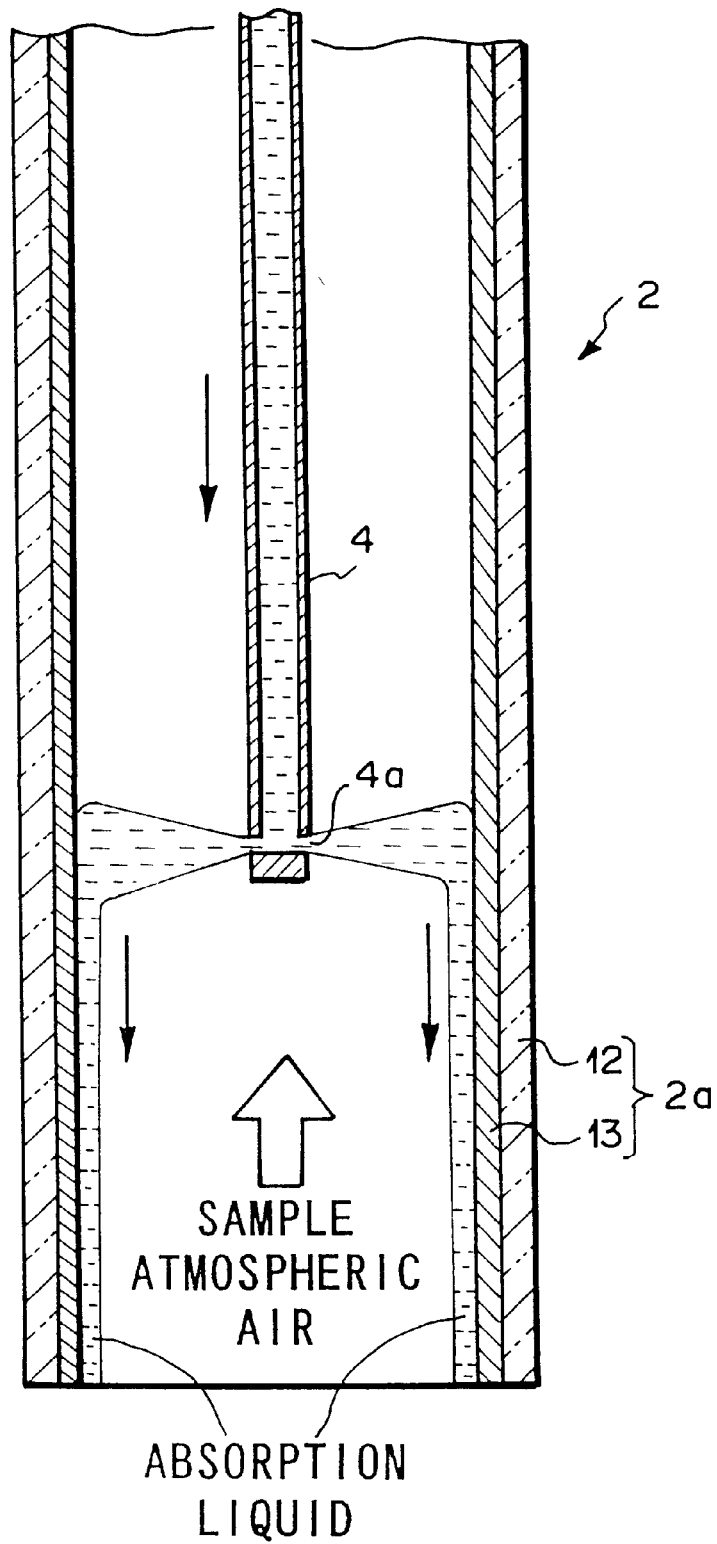
FIG. 6 is an enlarged cross-sectional view showing a denuder pipe and an absorption liquid supply tube of the denuder shown in FIGS. 4 and 5.

Here, the construction of the denuder 2 shown in FIG. 4 will be described in detail with reference to FIG. 6. FIG. 6 is an enlarged cross-sectional view showing the denuder pipe and the absorption liquid supply tube of the denuder shown in FIGS. 4 and 5.

As shown in FIG. 6, a photocatalyst thin film layer 13 is formed on the inner wall of a glass pipe 12 to form the denuder pipe 2a.

The glass pipe 12 is formed of a material which can transmit therethrough exciting light with low attenuation for exciting the photocatalyst. For example, quartz or pyrex is preferably used as the material of the glass pipe 12. According to the result of inventor's examination, it has been confirmed that the photocatalyst is optically excited when the light attenuation coefficient of the pipe wall of the glass pipe 12 at the specific wavelength is equal to 90% or less. Further, it has been confirmed that the photocatalyst is furthermore optically excited when the attenuation coefficient is equal to 50% or less, and the surface of the photocatalyst thin film layer 13 is more excellently made hydrophilic.

For the photocatalyst thin film layer 13 photocatalysis material is used which is optically excited by light having specific wavelengths (for example, ultraviolet rays) of artificial light emitted from a white light source such as a fluorescent lamp, a xenon lamp, a halogen lamp or the like, or by natural light from the sun, and from which the same components as the analysis components or components interfering with the analysis are little eluted into the absorption liquid. As the photocatalysis material, one of materials such as anatase type titanium oxide, zinc oxide (exciting wavelength: 378 nm), tin oxide (exciting wavelength : 344 nm), rutile type titanium oxide (exciting wavelength: 413 nm), etc. is preferably used which are efficiently activated by artificial light emitted from an ultraviolet-ray light source such as a UV lamp or the like. Particularly, titanium oxide such as the anatase type titanium oxide, the rutile type titanium oxide or the like is harmless and chemically stable, and thus it is suitable as the thin film layer material.

The photocatalyst thin film layer 13 may be formed as a single film by using one of the above photocatalysis materials, or as a composite film by using two or more of the above photocatalysis materials. It is preferable that the photocatalyst thin film layer 13 be transparent and have a thickness of 0.01 $\mu$m to 5 $\mu$m, more preferably 1 $\mu$m or less. Further, when the photocatalyst thin film layer 13 is designed to have a porous surface, the photochemical reaction efficiency with organic materials, etc. which adhere to the photocatalyst thin film layer 13 is enhanced.

Further, the nozzle 4a of the absorption liquid supply tube 4 is formed by sealing the tip end of the absorption liquid supply tube 4 and forming pores on the tube wall in the neighborhood of the sealed portion so that the absorption liquid is dispersed in at least two directions to be supplied to the surface of the inner wall of the denuder pipe 2a as shown in FIGS. 4 to 6. The absorption liquid supplied from the absorption liquid supply tube 4 is diffused onto the overall surface of the inner wall of the denuder pipe 2a to form a water membrane on the surface of the photocatalyst thin film layer 13, and flows from the upper side to the lower side on the surface of the inner wall of the denuder pipe 2a, whereby the analysis components can be collected at a high collection rate with high reproducibility. Any construction may be adopted for the nozzle 4a in so far as it allows most of the absorption liquid sprayed from each pore to reach the inner wall of the denuder pipe 2a, and the design of the pores such as the number of the pores, the diameter of each pore and the position of the pores, etc. may be freely determined.

The denuder 2 is disposed under such an environment that it is exposed to light having specific wavelengths which is emitted from a white light source or the sun and serves to optically excite the photocatalyst of the photocatalyst thin film layer 13 formed on the inner wall of the denuder pipe 2a.

Figure 7:
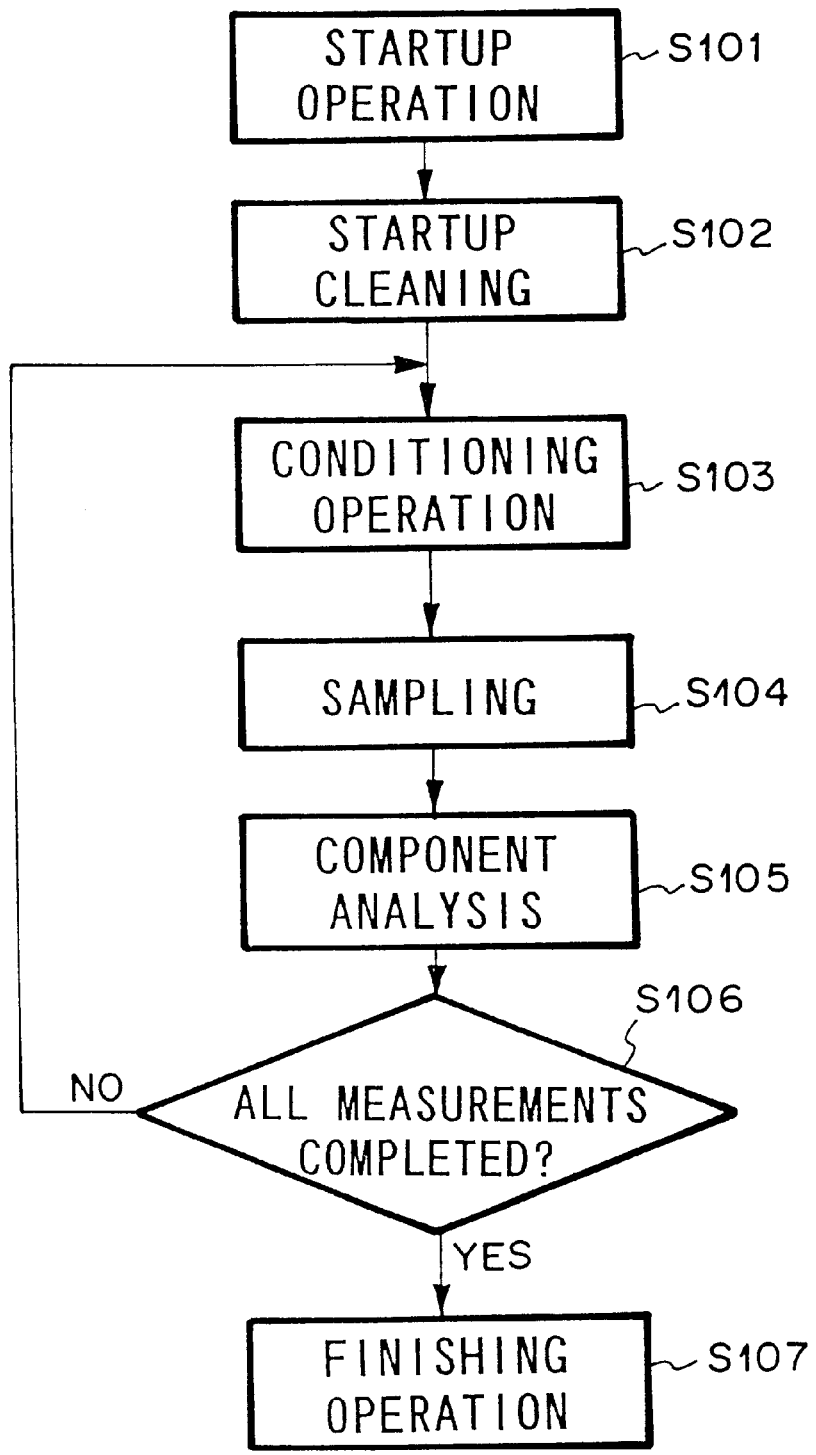
FIG. 7 is a flow chart showing an analysis process of a gas analysis method according to the first mode.

Next, a gas analysis method using the gas analysis apparatus of this mode will be described with reference to FIGS. 4 and 7. FIG. 7 is a flow chart showing the analysis process of the gas analysis method of this mode.

In a first step, a startup operation is carried out (S101). That is, the first flow-path switching valve 16 and the second flow-path switching valve 24 are switched to flow paths indicated by broken lines to discharge the residual absorption liquid in the denuder 2 from a discharge port of the second flow-path switching valve 24. Further, the third flow-path switching valve 18 is switched to a flow path indicated by a broken line, the third liquid feeding pump 20 is actuated to feed the eluent liquid to the concentrating column 19 to make the analysis components remaining in the concentrating column 19 be eluted into the eluent liquid, thereby removing the analysis components from the concentrating column 19.

In a second step, a startup cleaning operation is carried out (S102). That is, the first liquid feeding pump 14 is actuated to supply fresh absorption liquid from the absorption liquid supply tube 4 into the denuder 2. This supply operation is continued for a predetermined time to clean (wash) the inside of the denuder 2 with the fresh absorption liquid.

In a third step, a conditioning operation is carried out (S103). That is, the suction pump 15 is actuated to feed the sample atmospheric air from the sample atmospheric air supply tube 7 of the denuder 2 into the sample atmospheric air exhaust tube 5 via the denuder pipe 2a. This air feeding operation is continued for a predetermined time in order to balance the concentration of the analysis components contained in the sample atmospheric air flowing in the denuder pipe 2a, with that contained in the absorption liquid flowing down on the inner wall of the denuder pipe 2a.

In a fourth step, a sampling operation is carried out (S104). First, the first flow-path switching valve 16 and the third flow-path switching valve 18 are switched to flow paths indicated by solid lines. The suction pump 15 is thereafter actuated to feed the sample atmospheric air from the sample atmospheric air supply tube 7 into the denuder 2, and also the first liquid feeding pump 14 is actuated to feed the absorption liquid along the inner wall of the denuder pipe 2a. Further, the second liquid feeding pump 17 is actuated to feed to the concentrating column 19 the absorption liquid which is discharged from the absorption liquid discharging tube 6, and the analysis components collected by the absorption liquid are adsorbed by the concentrating column 19.

In a fifth step, an analysis of the analysis components is made (SI05). First, the first flow-path switching valve 16 and the third flow-path switching valve 18 are switched to the flow paths indicated by the broken lines (the flow-path switching valves 16 and 18 are kept in the same positions as the third step). The eluent liquid is fed to the concentrating column 19 by the third liquid feeding pump 20 to elute into the elute liquid the analysis components which are adsorbed by the concentrating column 19, and then the elute liquid (eluate) containing the analysis components is fed to the separation column 21. The analysis components are separated from each other in the separation column 21, and then the analysis components thus separated are made to flow through the suppressor 22 and the conductivity detector 23 in this order. The component detection is carried out in the conductivity detector 23, and the time-variation of the detection intensity of the detector is taken into a data processor/controller (not shown). On the basis of the collected data, the data processor/controller detects the variation of the detection intensity which is caused by the analysis components (when plural components are analyzed, assignments (identification) of the respective analysis components are carried out), and the concentration of each component is automatically calculated on the basis of calibration curve data which has been stored in advance.

When the measurement is continuously carried out at multiple times, the third to fifth steps are repeated the number of times corresponding to the demanded number of times of the measurement via a sixth step (S106). In this case, the third and the fifth steps can be carried out simultaneously, and thus the continuing time of the third step is equal to the component analysis time of the fifth step. After all the measurements are completed, the process goes to a next step via the sixth step (S106).

In a seventh step, a finishing operation is carried out (S107). First, the second liquid feeding pump 17 is stopped, and the first flow-path switching valve 16 is switched to the flow path indicated by the broken line to discharge the absorption liquid remaining in the denuder 2 from the discharge port of the second flow-path switching valve 24. Subsequently, only the second flow-path switching valve 24 is switched to the flow path indicated by the solid line and the first liquid feeding pump 14 is actuated to feed the absorption liquid into the denuder 2 and fill the inside of the denuder 2 with the absorption liquid. Thereafter, the overall gas analysis apparatus 1 containing the ion chromatograph 3 and the data processor/controller (not shown) is stopped. With this state being kept, the denuder 2 is disposed under such an environment that it is exposed to artificial light which contains light having specific wavelengths for exciting the photocatalyst thin film layer 13 and emitted from a fluorescent lamp or the like, or natural light emitted from the sun.

The seventh step (finishing operation) may be limited to the step of stopping the gas analysis apparatus 1. However, from inventor's test results, when the denuder 2 has been kept deactivated for a long term, it has been confirmed that reduction in wettability of the absorption liquid onto the inner wall of the denuder pipe 2a can be prevented more efficiently when the gas analysis apparatus is stopped while the denuder 2 is filled with the absorption liquid, than when the apparatus is stopped while the denuder 2 is empty.

As described above, the photocatalyst thin film layer 13 which is optically excited by irradiation of light is formed on the inner wall of the glass pipe 12. Therefore, when the denuder 2 is disposed under such an environment that it is exposed to light having specific wavelengths which excite the photocatalyst thin film layer 13, the photocatalyst thin film layer 13 is excited by the light at all times, and thus the surface of the photocatalyst thin film layer 13 is made super-hydrophilic to the extent that the contact angle with water is equal to about zero degrees. Therefore, organic components, etc. which adhere to the surface of the photocatalyst thin film layer 13 are immediately washed out by the adsorption liquid, and the surface of the photocatalyst thin film 13 is self-cleaned.

Further, as described in the above, in the sixth step (finishing operation), the denuder 2 is disposed under such an environment that it is exposed to light having wavelengths which can excite the photocatalyst thin film layer 13, so that the organic components, etc. adhered to the surface of the photocatalyst thin film layer 13 are liberated and removed into the absorption liquid filled in the denuder 2. Therefore, even when the gas analysis apparatus 1 is at rest, the surface of the photocatalyst thin film layer 13 is self-cleaned.

The foregoing description is made in the case where the gas analysis apparatus 1 is stopped while the denuder 2 is filled with the absorption liquid. When the gas analysis apparatus 1 is stopped when no absorption liquid is filled in the denuder 2, the organic components, etc. adhering to the surface of the photocatalyst thin film layer 13 can be easily washed out by cleaning the inside of the denuder 2 with the absorption liquid in the second step (startup cleaning). As a result, the surface of the photocatalyst thin film layer 13 is self-cleaned.

As described above, the photocatalyst thin film layer 13 is optically excited to be made super-hydrophilic, thereby self-cleaning the surface thereof. Therefore, uniform wettability of the absorption liquid to the surface of the inner wall of the denuder pipe 2a is kept, so that the time-variation of the collection efficiency of the analysis components can be suppressed, and the precision of concentration measurement of the analysis components can be kept. Further, since it is unnecessary to periodically carry out maintenance and cleaning on the denuder 2, the burden imposed on users by the gas analysis apparatus 1 can be reduced.

Further, in the gas analysis apparatus 1 of this mode, the absorption liquid which absorbed the analysis components in the denuder 2 is directly fed to the concentrating column 19 so as to directly perform concentration of the analysis components. Therefore, the analysis time can be reduced to be less as compared with the case where the analysis components are dissolved in absorption (suction) liquid stocked in an impinger or the like, and then the absorption liquid is fed to a concentrating column in a separate step as in the case of the conventional absorption (suction) method.

In addition, in this mode, the water membrane of the absorption liquid is formed on the overall surface of the inner wall of the denuder pipe 2a to absorb the analysis components, so that the analysis components can be efficiently absorbed even when the amount of the absorption liquid is small. Accordingly, the ratio of an amount of the analysis components which already has been contained in the absorption liquid prior to entering the denuder 2 relative to an amount of the analysis components which is just absorbed by the absorption liquid in the denuder 2 can be reduced, and thus the analysis precision in this mode can be enhanced, for example 5 to 10 times, as compared with the conventional suction method.

Figure 1:
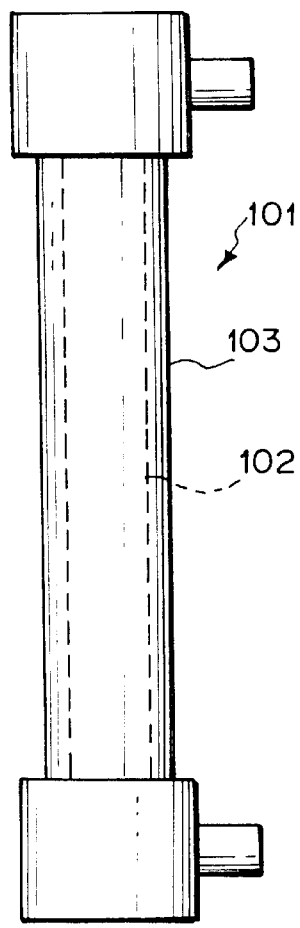
FIG. 1 is a diagram showing the construction of a diffusion scrubber body of a conventional gas analysis apparatus.
Figure 3:
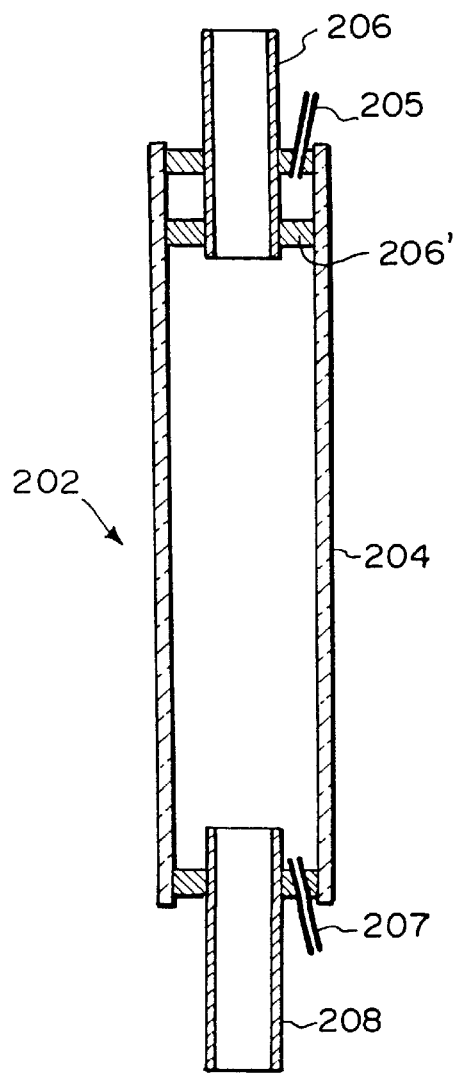
FIG. 3 is an enlarged cross-sectional view of the denuder body shown in FIG. 2.
Figure 2:
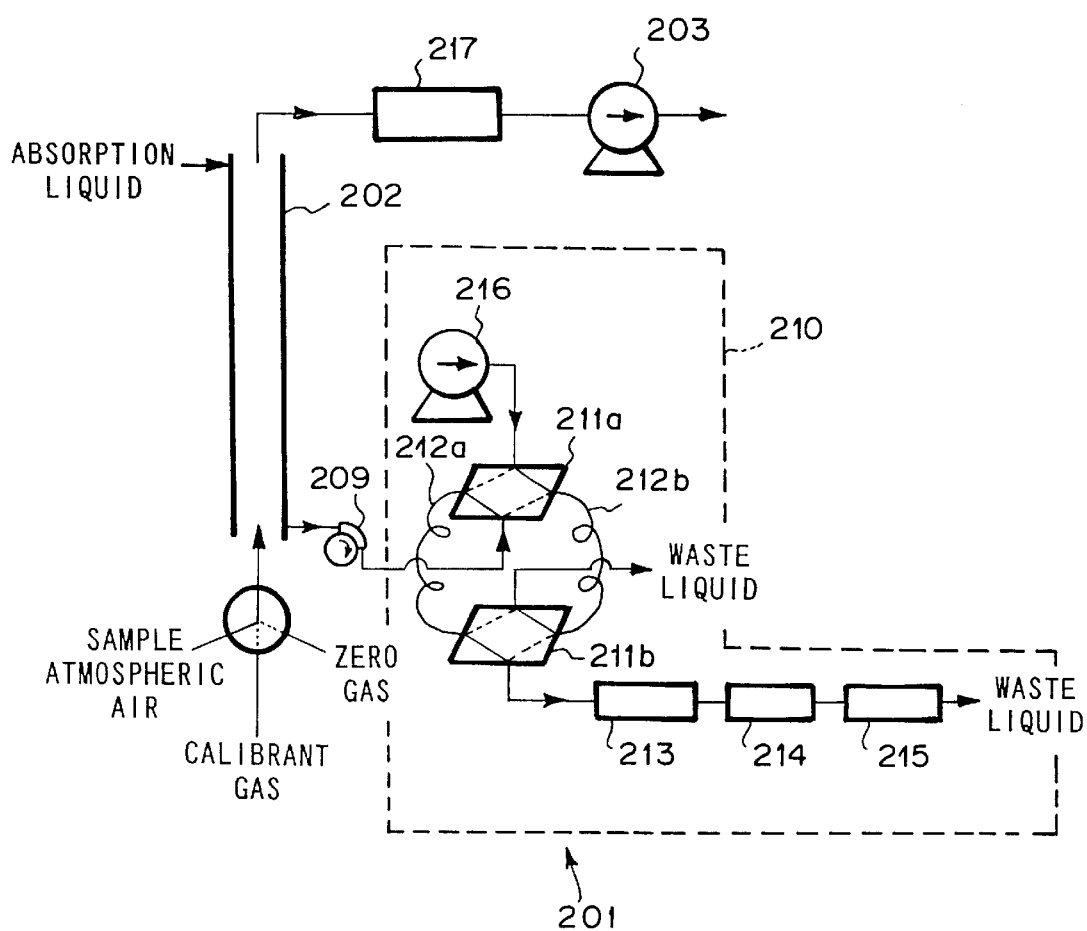
FIG. 2 is a diagram showing the overall construction of the conventional gas analysis apparatus using a wet denuder method.

Furthermore, comparing the gas analysis apparatus 1 of this mode with the conventional diffusion scrubber method, the sample atmospheric air and the absorption liquid are brought into indirect contact with each other via the inner pipe 102 of the gas permeable tube in the diffusion scrubber method as shown in FIG. 1, whereas the sample atmospheric air is brought into direct contact with the absorption liquid fed along the inner wall of the denuder pipe 2a in the gas analysis apparatus 1 of this mode as shown in FIG. 6, so that a high collection rate can be achieved for various analysis components. Further, in the diffusion scrubber method, the sample atmospheric air is fed through the inside of the slender inner pipe 102. On the other hand, in this mode, the sample atmospheric air is fed through the denuder pipe 2a, and the contact area between the sample atmospheric air and the absorption liquid is larger, and thus the analysis components can be collected at a higher collection rate in this mode than in the conventional diffusion scrubber method.

Still furthermore, in the diffusion scrubber method, a delay occurs when the analysis components are diffused in the gas permeable membrane, and an analysis result of analysis components which were collected in a previous measurement is detected in a subsequent measurement (i.e., it has a "memory effect"). However, in this mode, no "memory effect" due to the delay of the diffusion in the permeable membrane occurs, because the sample atmospheric air and the absorption liquid are brought into direct contact with each other.

Figure 8:
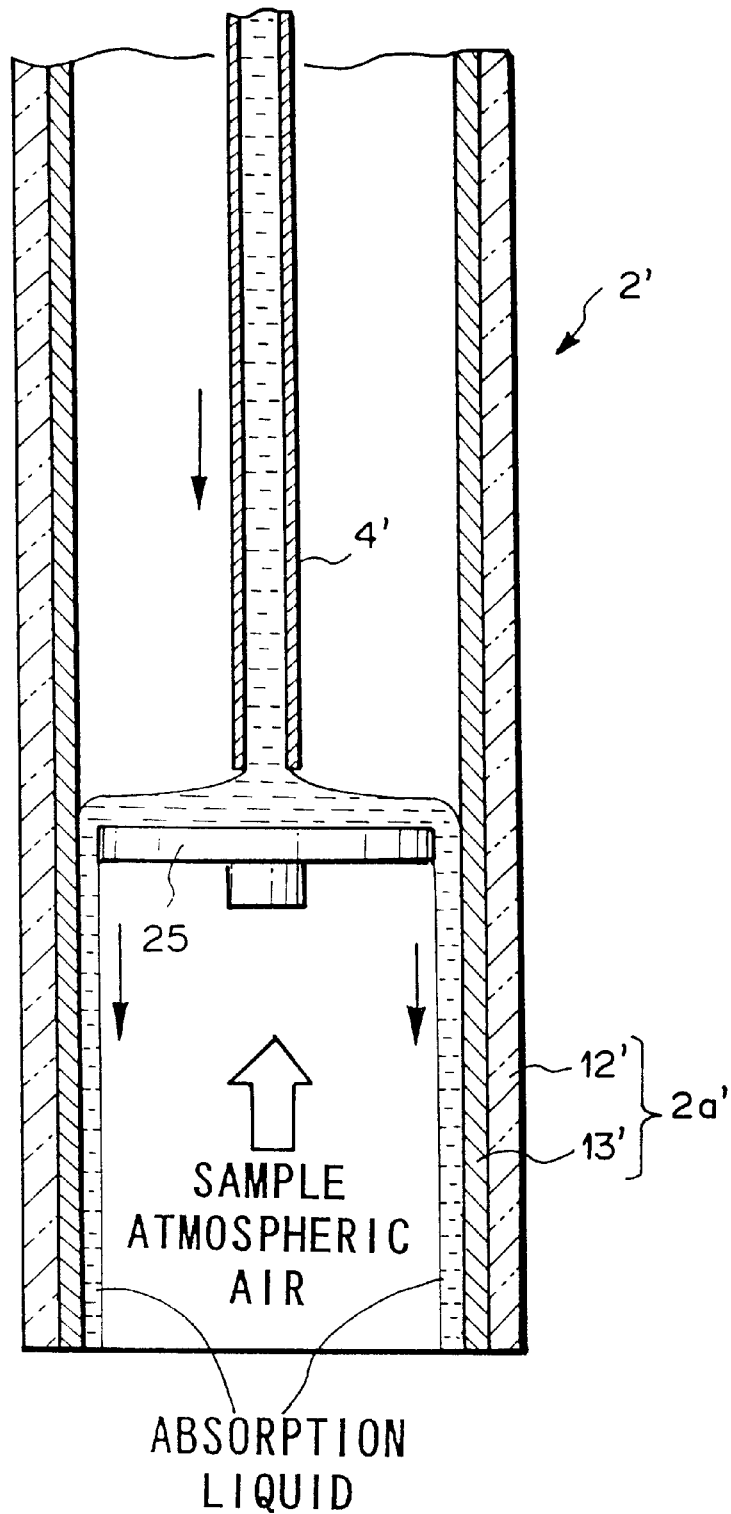
FIG. 8 is an enlarged cross-sectional view of a modification of the denuder shown in FIG. 4.

In the denuder 2 of this mode, the nozzle 4a is provided at the tip of the absorption liquid supply tube 4 and the absorption liquid is sprayed from the nozzle 4a to the inner wall of the denuder pipe 2a as shown in FIG. 6. However, it may be modified to a denuder 2' shown in FIG. 8 in which a diffusion plate 25 is disposed just below an absorption liquid supply tube 4'. The outer diameter of the diffusion plate 25 is set to be slightly smaller than the inner diameter of the denuder pipe 2a', and a gap through which the absorption liquid and the sample atmospheric air pass is formed between the outer edge of the diffusion plate 25 and the inner wall of the denuder pipe 2a'. The diffusion plate 25 is preferably formed of a material from which only a very small amount of the same components as the analysis components or components interfering with the analysis are eluted, and fluororesin or the like is preferable. The construction of a glass pipe 12' and the construction of a photocatalyst thin film layer 13' are the same as those of the gas analysis apparatus 1 shown in FIG. 4.

With the above construction, when the absorption liquid is fed from the absorption liquid supply tube 4' onto the diffusion plate 25, the absorption liquid is diffused toward the overall outer peripheral edge of the diffusion plate 25, and falls down to the lower side of the denuder pipe 2a' along the surface of the inner wall of the denuder pipe 2a', whereby a water membrane of the absorption liquid is formed on the overall surface of the inner wall of the denuder pipe 2a'. Therefore, the analysis components can be collected at a high collection rate with high reproducibility.

Furthermore, in the ion chromatograph 3 of this mode, the concentrating column 19 is used to achieve high detection sensitivity as shown in FIG. 4. However, when the high detection sensitivity is unnecessary, a sample loop comprising a tube having a fixed capacity as used in the gas analysis apparatus 101 shown in FIG. 1 may be used in place of the concentrating column 19.

The concentrating column 19 has a large pressure loss, and the second liquid feeding pump 17 shown in FIG. 4 is needed to feed the absorption liquid to the concentrating column 19. However, when the pressure loss of the pipe extending from the absorption liquid exhaust tube 6 to the analysis portion is small, for example when the sample loop is used in place of the concentrating column 19, the absorption liquid is fed to the component detection apparatus by using only gravitational force. Therefore, the second liquid feeding pump 17 is unnecessary.

In this mode, the ion chromatograph 3 is used as the component detection apparatus for detecting the gas components collected by the denuder 2. However, the component detection apparatus which is applicable to the gas analysis apparatus 1 is not limited to the liquid chromatograph such as the ion chromatograph 3 or the like, and it is preferable to use a component detection apparatus in accordance with the component/the component group which is an analysis target.

Figure 9:
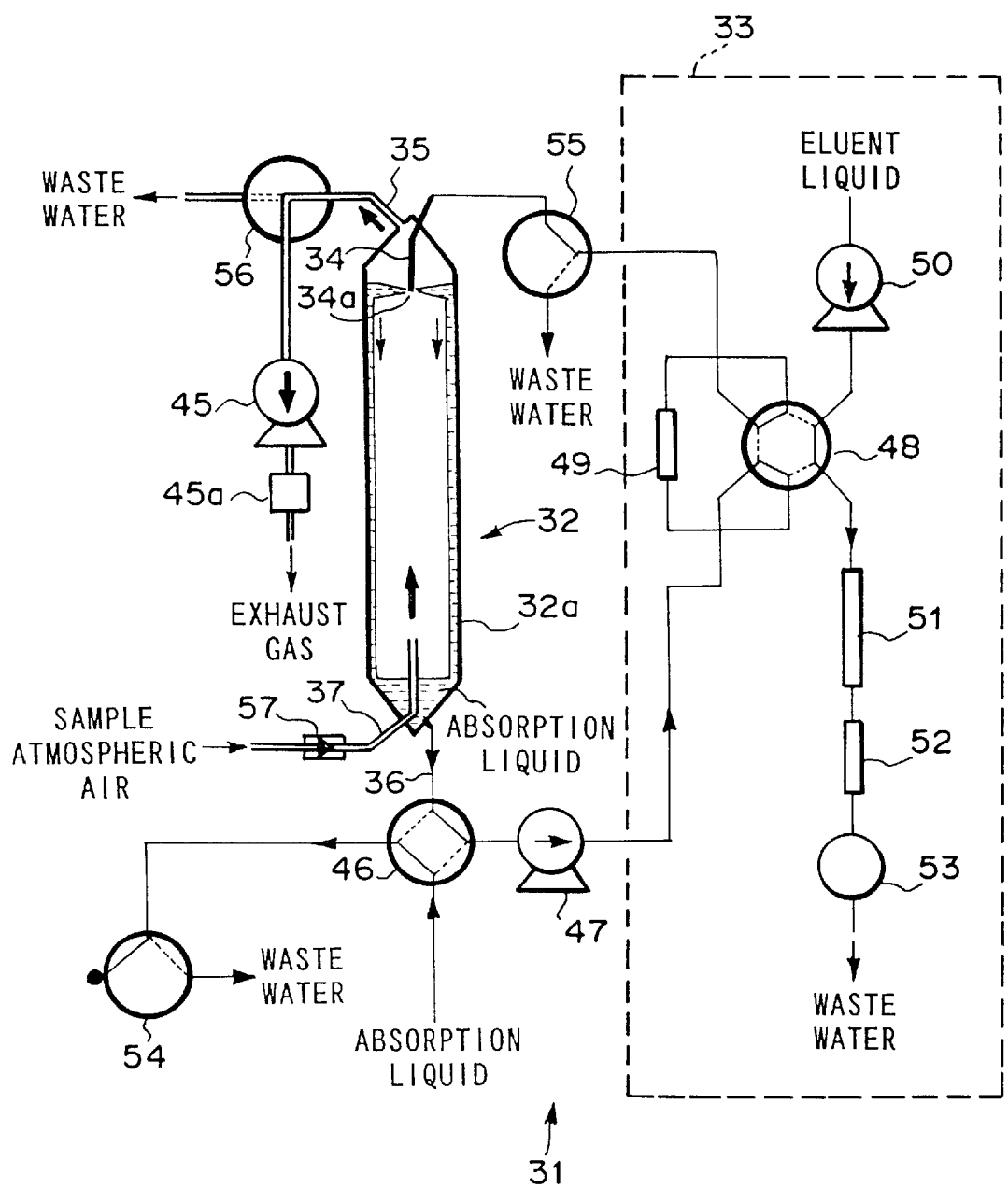
FIG. 9 is a diagram showing the construction of a second mode of the gas analysis apparatus of the present invention.

FIG. 9 is a diagram showing an alternative embodiment of the gas analysis apparatus of the present invention.

In the gas analysis apparatus 1 shown in FIG. 4, the absorption liquid which is fed to the denuder 2 and passed through the concentrating column 19 is wasted. On the other hand, in the gas analysis apparatus shown in FIG. 9, the absorption liquid which is discharged from the denuder 32 and passed through the condensing column 49 is passed through a fourth flow-path switching valve 55, and fed from the absorption liquid supply tube 34 into the denuder 32 again. The absorption liquid is circulated in an absorption liquid circulating system between the denuder 32 and the concentrating column 49. Fresh absorption liquid is supplied into the absorption liquid circulating system between the denuder 32 and the concentrating column 49 through the first flow-path switching valve 46. Further, in the gas analysis apparatus 31 of this mode, a fifth flow-path switching valve 56 is disposed in the flow path between the sample atmospheric air exhaust tube 35 and the suction pump 45. A check valve 57 is disposed in the sample atmospheric air supply tube 37.

The same construction of each element of the gas analysis apparatus shown in FIG. 4 is applied to each element of the denuder 32, the denuder pipe 32a, the ion chromatograph 33, the absorption liquid supply tube 34, the nozzle 34a, the sample atmospheric air exhaust tube 35, the absorption liquid exhaust tube 36, the sample atmospheric supply tube 37, the connection joint (not shown), each seal member (not shown), the glass pipe (not shown), the photocatalyst thin film layer (not shown), the suction pump 45, the flow-rate controller 45a, the first flow-path switching valve 46, the second liquid feeding pump 47, the third flow-path switching valve 48, the condensing column 49, the third liquid feeding pump 50, the separation column 51, the suppressor 52, the conductivity detector 53 and the second flow-path switching valve 54.

In the gas analysis apparatus 1 shown in FIG. 4, the first liquid feeding pump 14 is used to supply the absorption liquid into the denuder 2. However, since the absorption liquid is circulated between the denuder 32 and the concentrating column 49 in the gas analysis apparatus 31 of this mode as described above, a liquid feeding pump corresponding to the first liquid feeding pump 14 is not provided.

Figure 10:
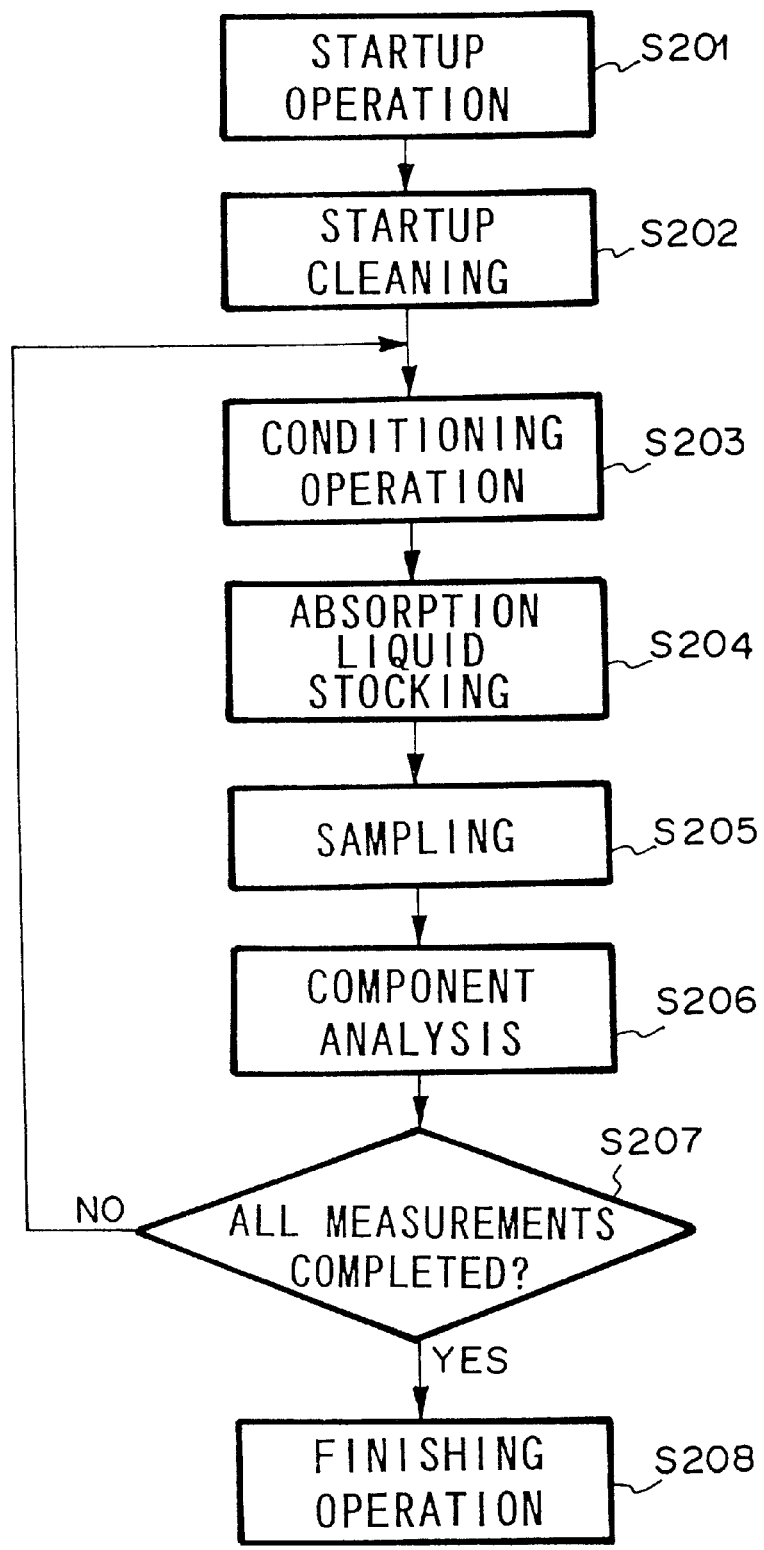
FIG. 10 is a flow chart showing an analysis process of a gas analysis method according to the second mode.

Next, the gas analysis method using the gas analysis apparatus 31 of this mode described above will be described with reference to FIGS. 9 and 10. FIG. 10 is a flow chart showing an analysis process of the gas analysis method of this mode.

In a first step, a startup operation is carried out (S201). First, the flow-path switching valves 48, 54 and 56 are switched to flow paths indicated by broken lines to discharge the absorption liquid remaining in the denuder 32 from the discharge port of the second flow-path switching valve 54. Further, the third flow-path switching valve 48 is switched to a flow path indicated by a broken line, and eluent solution is fed into the concentrating column 49 by the third liquid feeding pump 50 to elute the analysis components remaining in the concentrating column 49 into the eluent solution, thereby removing the analysis components from the concentrating column 49. Further, the fourth flow-path switching valve 55 is switched to a flow path indicated by a broken line, and the second liquid feeding pump 47 is actuated to feed the absorption liquid, whereby the absorption liquid remaining in the pipe extending from the second liquid feeding pump 47 to the fourth flow-path switching valve 55 is substituted by fresh absorption liquid.

In a second step, a startup washing (cleaning) operation is carried out (S202). That is, the fourth flow-path switching valve 55 is switched to a flow path indicated by a solid line, and the second liquid feeding pump 47 is actuated to supply fresh absorption liquid from the absorption liquid supply tube 34 into the denuder 32. This state is continued for a predetermined time to wash the inside of the denuder 32 with the fresh absorption liquid.

In a third step, a conditioning operation is carried out (S203). That is, the fifth flow-path switching valve 56 is switched to a flow path indicated by a solid line, and the suction pump 45 is actuated to feed the sample atmospheric air from the sample atmospheric air supply tube 37 of the denuder 32 into the sample atmospheric air exhaust tube 35 via the denuder pipe 32a. This feeding state is continued for a predetermined fixed time in order to balance the concentration of the analysis components contained in the sample atmospheric air flowing in the denuder pipe 32a with that contained in the absorption liquid flowing down on the inner wall of the denuder pipe 32a.

In a fourth step, an absorption liquid stocking operation is carried out (S204). That is, the suction pump 45 is stopped, and the second flow-path switching valve 54 is switched to the flow path indicated by a solid line to stock a predetermined amount of absorption liquid (preferably, 5 ml or less) is stocked at the bottom portion of the denuder 32.

In a fifth step, a sampling operation is carried out (S205). First, the first flow-path switching valve 46 and the third flow-path switching valve 48 are switched to the flow paths indicated by the solid line. Subsequently, the suction pump 45 is actuated to feed the sample atmospheric air from the sample atmospheric supply tube 37 into the denuder 32, and the second liquid feeding pump 47 is actuated, whereby the absorption liquid stocked at the bottom portion of the denuder 32 is fed to the concentrating column 49. After the analysis components contained in the absorption liquid are removed, the absorption liquid is fed from the absorption liquid supply tube 34 to the denuder 32 again, and brought into contact with the sample atmospheric air, whereby the analysis components are absorbed by the absorption liquid. Thereafter, the absorption liquid containing the analysis components is fed to the concentrating column 49 again, and the analysis components collected by the absorption liquid is adsorbed by the concentrating column 49. Through this step, the collection of the analysis components into the absorption liquid with the analysis components concentrated in the absorption liquid is performed.

In a sixth step, a component analysis is carried out (S206). First the first flow-path switching valve 46 and the third flow-path switching valve 48 are switched to the flow paths indicated by the broken lines (the flow-path switching valves 46, 48 are set in the same positions as the third step). The eluent liquid is fed to the concentrating column 49 by the third liquid feeding pump 50 to elute the concentrated analysis components into the eluent liquid, and then the eluent liquid (eluate) containing the analysis components is fed to the separation column 51. After the analysis components are separated from each other in the separation column 51, the analysis components are made to flow through the suppressor 52 and the conductivity detector 53 in this order. In this case, the component detection is performed in the conductivity detector 53 to take time-variation of detection intensity of the detector into the data processor/controller (not shown). The data processor/controller detects the variation of the detection intensity due to the analysis components on the basis of the collected data (when plural analysis components are analyzed, the assignments (identification) of the respective components are carried out), and automatically calculate the concentration of each component on the basis of calibration curve data which are input in advance.

When the measurement is continuously carried out over multiple times, the third to sixth steps are repeated at the number of times which corresponds to the necessary frequency of the measurement via a seventh step (207). In this case, the third and sixth steps are carried out simultaneously, and the continuing time of the third step is set to be equal to the component analysis time of the sixth step. After all the measurements are completed, the process goes to an eighth step (S208) via the seventh step (207).

In the eighth step (S208), a finishing operation is carried out. First, the second liquid feeding pump 47 is stopped, and the flow-path switching valves 46, 54 and 56 are switched to the states indicated by the broken lines to discharge the absorption liquid remaining in the denuder 32 from the discharge port of the flow-path switching valve 54. Subsequently, the second flow-path switching valve 54 is switched to the flow path indicated by the solid line, and the second liquid feeding pump 47 is actuated to feed the absorption liquid into the denuder 32 and fill the denuder 32-with the absorption liquid. Thereafter, the overall gas analysis apparatus 31 containing the ion chromatograph 33 and the data processor/controller (not shown) is stopped. With this state being kept, the denuder 32 is disposed under such an environment that it is exposed to artificial light which is emitted from a fluorescent lamp or the like and which has the wavelengths for optically exciting the photocatalyst thin film layer, or it is exposed to natural light from the sun.

In the eighth step, the stop of the gas analysis apparatus 31 may be merely carried out. However, from results of inventor's test, when the denuder 32 has been kept deactivated for a long term, it has been confirmed that reduction in wettability of the absorption liquid onto the inner wall of the denuder pipe 32a can be prevented more efficiently when the gas analysis apparatus is stopped while the denuder 32 is filled with the absorption liquid than when the apparatus is stopped while the denuder is empty.

In the gas analysis apparatus 1 of the first mode, since the fresh absorption liquid is fed into the denuder 2 at all times, the liquid flow velocity of the second liquid feeding pump 17 is required to be suppressed in order to reduce the amount of the absorption liquid used for one measurement. On the other hand, in the gas analysis apparatus 31 of this mode, the absorption liquid stocked at the bottom portion of the denuder 32 is circulatively fed as described above, the amount of the absorption liquid itself used for the measurement is kept constant irrespective of the flow velocity of the liquid. Accordingly, the flow velocity of the absorption liquid can be set to any value within such a range that no capturing loss of the analysis components occurs in the concentrating column 49. In this case, if the liquid flow velocity is set to a large value, the circulation of the absorption liquid is carried out at a high speed. Therefore, the analysis components in the sample atmospheric air are efficiently absorbed and the "memory effect" in the denuder 32 can be suppressed.

Next, a modification of the gas analysis apparatus 31 shown in FIG. 9 will be described.

Figure 11:
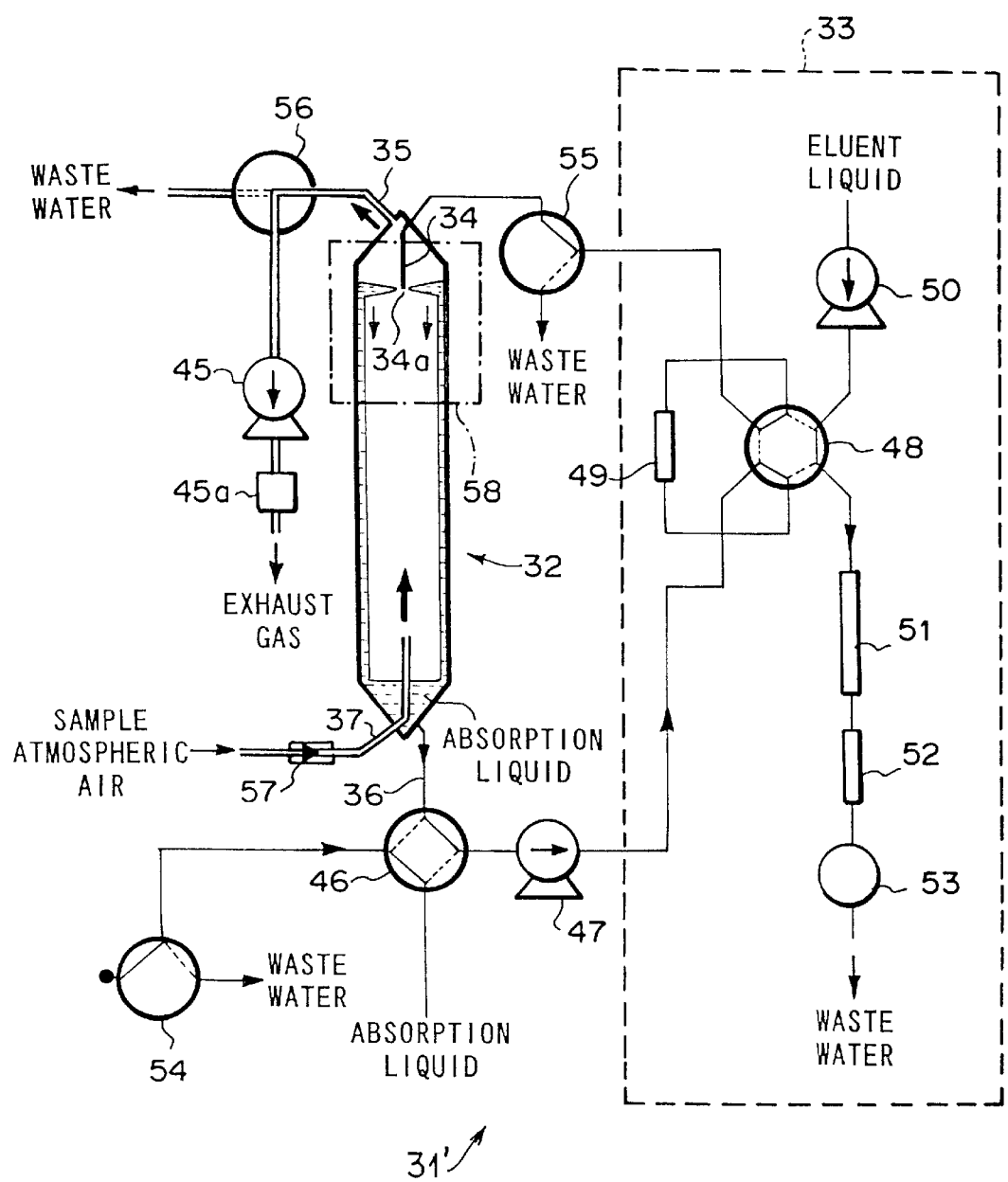
FIG. 11 is a diagram showing the construction of a modification of the gas analysis apparatus shown in FIG. 9.

FIG. 11 is a diagram showing the construction of a modification of the gas analysis apparatus 31 shown in FIG. 9. As shown in FIG. 11, a gas analysis apparatus 31' of this modification is provided, on the upper portion of the denuder 32, with a cooling apparatus 58 for cooling the denuder 32 in addition to the respective elements of the gas analysis apparatus 31 shown in FIG. 9. The cooling apparatus 58 can be controlled to cool the denuder 32 so that the temperature of the inside of the denuder 32 is equal to 10° C. or less.

Vaporization of the absorption liquid can be suppressed by cooling a part or the overall of the denuder 32 with the cooling apparatus 58, so that reduction of the collection efficiency of the analysis components in the sample atmospheric air can be suppressed and the analysis precision can be enhanced. In addition, the analysis components are captured when water vapor is agglomerated, and thus the collection rate can be also be enhanced.

According to the inventor's experimental results, it has been confirmed that when the temperature of the inside of the denuder 32 is set between 0° C. to 10° C., the analysis precision of the analysis components is enhanced. Further, it has been confirmed that when the temperature of the denuder 32 is set to 5° C., the analysis precision of the analysis components is best.

The application of the cooling apparatus 58 is not limited to the modification of the gas analysis apparatus 31' of this modification. It may be likewise applied to the gas analysis apparatus 1 shown in FIG. 4 and the gas analysis apparatus 61 shown in FIG. 12.

FIG. 12 is a diagram showing the construction of a third embodiment of gas analysis apparatus of the present invention.

As shown in FIG. 12, in the gas analysis apparatus 61 of this mode, an exciting light source 88 is disposed in the neighborhood of the denuder 62. The exciting light source 88 can emit light of specific wavelengths (for example, ultraviolet rays) having high intensity to excite the photocatalyst thin film layer (not shown), and it can be turned on continuously or intermittently. It is preferable that the exciting light source 88 generate no ozone when it emits light, and also that the intensity of the light at wavelengths below the exciting wavelengths of the photocatalyst thin film layer (not shown) below, whereby harmful gas can be prevented from occurring in the gas analysis apparatus 61 for operator safety.

The same construction as for each element of the gas analysis apparatus 31 shown in FIG. 9 is applied to each of a denuder 62, a denuder pipe 62a, an ion chromatograph 63, an absorption liquid supply tube 64, a nozzle 64a, a sample atmospheric air exhaust tube 65, an absorption liquid exhaust tube 66, a sample atmospheric supply tube 67, a connection joint (not shown), each seal member (not shown), a glass pipe (not shown), a photocatalyst thin film layer (not shown), a suction pump 75, a flow rate controller 75a, a first flow-path switching valve 76, a second liquid feeding pump 77, a third flow-path switching valve 78, a concentrating column 79, a third liquid feeding pump 80, a separation column 81, a suppressor 82, a conductivity detector 83, a second flow-path switching valve 84, a fourth flow-path switching valve 85, a fifth flow-path switching valve 86 and a check valve 87, and the detailed description of these elements is omitted.

According to the gas analysis apparatus 61 thus constructed, the analysis of the analysis components is carried out in the same manner as the gas analysis method using the gas analysis apparatus 31 of the second embodiment (see FIG. 9). The details of the analysis step are the same as the first through eighth steps which are described with reference to FIG. 10. However, according to the gas analysis method of this mode, in the third to sixth steps, which are repeated at a necessary measurement frequency, the two measurements of the fifth step (sampling), one of which is carried out while the exciting light source 88 is turned on, and the other of which is carried out while the exciting light source 88 is turned off, are carried out as a pair of measurements.

When the fifth step (sampling) is carried out while the exciting light source 88 is turned off, the photocatalyst thin film layer is activated to the extent that the soil on the inner surface of the denuder pipe 62a is prevented (self cleaning), and only the water-soluble analysis components in the sample atmospheric air are collected by the absorption liquid. On the other hand, when the fifth step (sampling) is carried out while the exciting light source 88 is turned on, the photocatalyst thin film layer is very intensely activated to the extent that components such as NO, $NO_2$, etc. which are little soluble in the absorption liquid if it is not modified are oxidized into nitrous acid, etc. which are soluble in the absorption liquid.

Accordingly, the measurement of the analysis components is carried out under the two conditions that the sampling is carried out while the exciting light source 88 is turned on and that the sampling is carried out while the exciting light source 88 is turned off, whereby the water-soluble and water-insoluble analysis components can be collected. Therefore, the analysis on various types of analysis components can be carried out.

Further, the application of the exciting light source 88 is not limited to the gas analysis apparatus 61 of this mode, and it may be likewise applied to the gas analysis apparatus 1 shown in FIG. 4 and the gas analysis apparatus 31 shown in FIG. 9.

In the gas analysis apparatus 61 shown in FIG. 12, a reflection plate (not shown) for reflecting exciting light may be provided so as to confront the exciting light source 88 with the denuder 62 interposed therebetween, whereby the activation efficiency of the photocatalyst thin film layer can be enhanced.

Further, the denuder 62 and the exciting light source 88 may be accommodated in a container whose inner wall is formed of mirror (not shown). In this case, the activation efficiency of the photocatalyst thin film layer can be enhanced. In addition, even if harmful gas occurs, the gas does not leak from the container, and the safety of the operators can be kept.

Next, preferred embodiments of the gas analysis apparatus of the present invention will be described with reference to the accompanying drawings.

An application of an embodiment of the gas analysis apparatus 1 of FIG. 4, etc. will be described.

The gas analysis apparatus 1 of this embodiment is a gas analysis apparatus for analyzing ammonia component in the atmospheric air, which uses as a detection apparatus an ion chromatograph 3 (DX120 produced by Dionex Corporation) in which the separation column 21 (Ion Pac CS12 produced by Dionex Corporation), the concentrating column 19 (Ion Pac CG12 produced by Dionex Corporation) and the suppressor 22 (CSRS-I produced by Dionex Corporation) are used.

Ultra-pure water was used as absorption liquid and 20 mM methanesulfonic acid solution is used as the eluent liquid. A pyrex glass pipe having a dimension of 12 mm in inner diameter, 16 mm in outer diameter and 600 mm in length was used as the glass pipe 12 of the denuder pipe 2a. The photocatalyst thin film layer 13 comprising a transparent porous film of 0.7 $\mu$m thickness which was formed of anatase type titanium oxide. The denuder 2 was disposed vertically, while the upper portion thereof which contained the absorption liquid supply tube 4 and the sample atmospheric air exhaust tube 5, were placed face up. Further, a 20 W fluorescent lamp was disposed in parallel to the denuder 2. The flow rate of the liquid in each of the first liquid feeding pump 14 and the second liquid feeding pump 17 was set to 0.5 ml/min, the flow rate of the liquid in the third liquid feeding pump 20 was set to 1 ml/min, and the flow rate of the air in the suction pump 15 was set to 1 l liter/min.

According to an estimation of the collection rate which was made by using standard gas in which the concentration of ammonia component was beforehand adjusted, the concentration of the ammonia component contained in the standard gas could be reproduced with 100% reproducibility when the flow rate of the suction pump 15 was equal to 2 liter/min or less.

The gas analysis was carried out according to the first to seventh steps described with reference to FIG. 7. The startup cleaning (washing) time in the second step (startup cleaning) was set to 20 minutes, the conditioning operation time in the third step (conditioning operation) was set to 10 minutes, the sampling time in the fourth step (sampling) was set to 5 minutes, and the component analysis time in the fifth step (component analysis) was set to 10 minutes. In the second and subsequent measurements in which the third step (conditioning operation) and the fifth step (component analysis) were carried out in parallel, the measurement was carried out at a period of 15 minutes (sampling of 5 minutes and component analysis of 10 minutes).

The detectable lower limit of the concentration of the ammonia component by the gas analysis apparatus 1 was equal to 0.02 ppbv. Further, in general, materials which are detected as ammonia contain some amines and, under the above condition, the amines could not be detected while separated from ammonia. However, by optimizing the separation column 21 and the eluent liquid of the ion chromatograph 3, the amines can be detected. The construction of the apparatus, the measurement condition, the measurement period and the detectable lower limit value are optimized on the basis of inventor's consideration, however, they are not limited to the above design and values.

Next, a further embodiment of the gas analysis apparatus 31 shown in FIG. 9, etc. will be described.

The gas analysis apparatus 31 of this embodiment is also used to analyze the ammonia component in the atmospheric air and, in the ion chromatograph 33, the separation column 51, the concentrating column 49 and the suppressor 52 as in the case of the first embodiment were used. The construction of the glass pipe and the photocatalyst thin film layer of the denuder pipe 32a, the absorption liquid, and the eluent liquid were the same as the first embodiment.

In this embodiment, the flow rate of the second liquid feeding pump 47 was set to 2 ml/min, the flow rate of the third liquid feeding pump 50 was set to 1 ml/min, and the flow rate of the suction pump 45 was set to 1 1 liter/min. The gas analysis was carried out according to the first to eighth steps described with reference to FIG. 10. The startup cleaning time in the second step (startup cleaning) was set to 20 minutes, the conditioning operation time in the third step (conditioning operation) was set to 10 minutes, the sampling time in the fifth step (sampling) was set to 5 minutes, and the component analysis time in the sixth step (component analysis) was set to 10 minutes. The stock amount of the absorption liquid at the bottom portion in the denuder 32 in the fourth step (absorption liquid stocking) was set to 2 ml (that is, the absorption liquid was fed for one minute). In the second and subsequent measurements in which the third step (conditioning operation) and the sixth step (component analysis) were carried out in parallel, the measurement could be performed at a period of 16 minutes (sampling: 5 minutes, absorption liquid stocking: one minute, and component analysis: 10 minutes).

The analysis result of the gas analysis apparatus 31 such as the detectable lower limit, etc. was the same as the first embodiment.

Next, an embodiment of the gas analysis apparatus 31' of the modification shown in FIG. 11 will be described.

The gas analysis apparatus 31' of this embodiment also aims to analyze the ammonia component in the atmospheric air and, in the ion chromatograph 33, the separation column 51, the concentrating column 49 and the suppressor 52 as in the case of the first embodiment were used. The construction of the glass pipe and the photocatalyst thin film layer of the denuder pipe 32a, the absorption liquid, and the eluent liquid were the same as the first embodiment.

In this embodiment, the component analysis was carried out according to the first to eighth steps of FIG. 10 under the same condition as described in the second embodiment. Further, in this embodiment, an upper one-third portion of the denuder 32 which extends from the upper portion thereof downwardly was cooled to 5° C. by the cooling apparatus 58 mounted at the upper portion of the denuder 32.

As described above, the upper portion of the denuder 32 was cooled by the cooling apparatus 58, and fine particles of salts were captured when the absorption liquid which was vaporized at the lower portion of the denuder 32 was cooled at the upper portion of the denuder 32 to be agglomerated. Therefore, in addition to the measurement result of the first and second embodiments, alkali metals such as Na, K, etc. could be detected. The collection rate of these materials was equal to about 70% of the collection rate based on the impinger method, however, reproducibility of the collection rate was obtained. Accordingly, if the collection rate is enhanced, the gas analysis apparatus 31' can be applied to the measurement of alkali metals.

Next, another embodiment of the gas analysis apparatus 1 shown in FIG. 4, etc. will be described.

The gas analysis apparatus 1 of this embodiment aims to analyze acidic gas components in the atmospheric air, which uses as a detection apparatus the ion chromatograph 3 (DX120 produced by Dionex Corporation) in which the separation column 21 (Ion Pac AS14 produced by Dionex Corporation), the concentrating column 19 (Ion Pac AG14 produced by Dionex Corporation) and the suppressor 22 (ASRS-1 produced by Dionex Corporation) are used.

In this embodiment, ultra-pure water was used as the absorption liquid, and solution of 4 mM sodium carbonate and 1.5 mM sodium bicarbonate was used as the eluent liquid. The gas analysis was carried out according to the first to sixth steps described with reference to FIG. 7. The startup cleaning (washing) time in the second step (startup cleaning) was set to 20 minutes, the conditioning operation time in the third step (conditioning operation) was set to 15 minutes, the sampling time in the fourth step (sampling) was set to 5 minutes, and the component analysis time in the fifth step (component analysis) was set to 10 minutes. The flow rate of the eluent liquid was set to 1.5 ml/min. The construction of each element of the denuder pipe 2a and the liquid flow rate in each liquid feeding pump were the same as the first embodiment.

As a result of the measurement by the gas analysis apparatus 1 of this embodiment, respective ions of fluoride, formic acid, acetic acid, chloride, nitrous acid, nitric acid and sulfuric acid were detected. Most of ions thus detected belonged to these acids, and some of the ions were salts thereof. Particularly, the nitrous acid ions were chemically changed from $NO_2$, and the sulfuric acid ions were chemically changed from $SO_2$.

As a result of the measurement using standard gas, hydrofluoric acid, formic acid, acetic acid, hydrochloric acid and nitric acid were collected substantially at 100% collection rate, however, $NO_2$ and $SO_2$ were collected at 40% and 80%, respectively. When hydrogen peroxide was added to the absorption liquid so that the concentration of hydrogen peroxide was equal to 100 ppm, the collection rate of $SO_2$ was enhanced to substantially 100%. The collection rate of $NO_2$ was enhanced to 60% when 5% isopropyl alcohol was used as the absorption liquid, and to 80% when 1 mM triethanolamine was used as the absorption liquid. At this time, the other components such as the ions of fluoride, formic acid, acetic acid and chloride each of which has a short retention time were incompletely collected by the concentrating column 19. The detectable lower limit of each component was equal to about 0.01 ppbv.

Further, the design which is suitable to analyze the acidic gas components in the atmospheric air like the gas analysis apparatus 1 of this embodiment is not limited to the gas analysis apparatus 1 shown in FIG. 4, and it may be applied to the gas analysis apparatus 31 shown in FIG. 9, the gas analysis apparatus 31' shown in FIG. 11 and the gas analysis apparatus 61 shown in FIG. 12. Particularly, in the case of the gas analysis apparatus 31' shown in FIG. 11, it has been confirmed that the collection rate of the components having a low collection rate is improved by about 5%.

An embodiment of the gas analysis apparatus of the mode shown in FIG. 12 will be described.

The gas analysis apparatus 61 of this embodiment aims to analyze acidic gas components in the atmospheric air as in the case of the gas analysis apparatus 1 of the previous embodiment and, in the ion chromatograph 63, the separation column 81, the concentrating column 79 and the suppressor 82 are used. A 10 W germicidal lamp was used as the exciting light source 88 for emitting ultraviolet rays. Further, a reflection plate having a mirror surface (not shown) was disposed at such a position as to confront the exciting light source 88 with the denuder 62 positioned therebetween, and another reflection plate was disposed on the back side of the exciting light source 88.

The gas analysis was carried out according to the first through eighth steps described with reference to FIG. 10. As described above, in the third through sixth steps which were repeated at a necessary measurement frequency, the two measurements of the fifth step (sampling), one of which was carried out while the exciting light source 88 was turned on, and the other of which was carried out while the exciting light source 88 was turned off, were carried out as a pair of measurements.

When the measurement was carried out while the exciting light source 88 was turned on, organic acids such as formic acid, acetic acid, etc. were decomposed by photochemical reaction, and thus the concentration of water-soluble analysis components was relatively reduced, so that the detection intensity of the water-soluble analysis components was reduced to about 50% of that obtained when the measurement was carried out while the exciting light source 88 was turned off. However, $SO_2$ and $NO_2$ which were collected at the collection rate of 80% and 40% respectively in the previous embodiment were collected substantially at 100% collection rate in this embodiment. Furthermore, NO which was little collected in the previous embodiment could be collected at a collection rate of about 70%. $NO_2$ and NO are detected as nitrous acid ions, and thus the total amount of $NO_2$ and NO in the sample atmospheric air can be determined from the detection result (i.e., each amount of $NO_2$ and NO in the sample atmospheric air cannot be determined).

As described above, by carrying out the measurement while the exciting light source 88 is turned on, most of acidic gas components can be detected even when ultra-pure water is used as the absorption liquid. Further, if the measurement on water-soluble analysis components and analysis components which are easily oxidatively decomposed under only a fluorescent lamp in the apparatus is carried out while the exciting light source 88 is turned off, and the measurement of analysis components to which the photochemical reaction is not sufficiently promoted under only a fluorescent lamp in the apparatus is carried out while the exciting light source 88 is turned on, many types of analysis components can be analyzed.

As described above, in the gas collection apparatus of the present invention, the photocatalyst thin film layer containing the photocatalyst which is optically excited to be made super-hydrophilic upon irradiation of light having specific wavelengths thereto is formed on the inner wall of the pipe through which the sample atmospheric air is fed and the absorption liquid for absorbing the analysis components is fed along the inner wall. The pipe is formed of a material which allows the light having the specific wavelengths to transmit therethrough, whereby organic components, etc. adhering to the surface of the photocatalyst thin film layer are easily washed out by the absorption liquid to self-clean the surface of the photocatalyst thin film layer. Therefore, uniform wettability of the absorption liquid to the surface of the inner wall of the pipe is kept, so that little time-variation of the collection rate of the analysis components occurs, and the precision of concentration measurement of the analysis components can be maintained.

By making the photocatalyst thin film layer porous, the photochemical reaction efficiency with organic components, etc. adhering to the surface of the photocatalyst thin film layer can be enhanced.

Further, by providing the cooling apparatus for cooling a part or all of the pipe, reduction of the collection rate of the analysis components in the sample atmospheric air can be prevented, and the analysis precision can be enhanced.

The gas analysis apparatus according to the present invention has the above-described gas collection apparatus and the component detection apparatus for detecting the analysis components contained in the absorption liquid which is fed along the inner wall of the pipe. The gas collection apparatus is disposed under such an environment that it is exposed to light having specific wavelengths which is emitted from a white light source or the sun and serves to optically excite the photocatalyst of the photocatalyst thin film layer formed on the inner wall of the pipe, whereby the surface of the photocatalyst thin film layer is self-cleaned and thus the uniform wettability of the absorption liquid to the surface of the inner wall of the pipe can be kept. Therefore, time-variation of the collection rate of the analysis components can be prevented, and the concentration measurement precision of the analysis components can be maintained. Further, it is unnecessary to periodically maintain and clean the gas collection apparatus, so that the burden on users can be reduced.

Further, the component detection apparatus is constructed by the concentrating means for concentrating the analysis components contained in the absorption liquid, desorption means for desorbing the analysis components concentrated by the concentrating means, and the detection means for detecting the analysis components. The analysis components are detected upon being concentrated, so that the detection intensity of the analysis components and the analysis precision can be enhanced.

Further, the absorption liquid from which the analysis components are removed when being passed through the concentrating means is circulatively fed into the gas collection apparatus, whereby the liquid flow velocity of the absorption liquid can be set to any value within such a range that no capturing loss of the analysis components occurs in the capturing and condensing means.

Still further, by providing an exciting light source for either continuously or intermittently irradiating the pipe with light having the specific wavelengths for exciting the photocatalyst, components such as NO, $NO_2$, etc., which are little dissolved in the absorption liquid if it is not modified, can be detected.

The gas analysis method of the present invention uses the gas analysis apparatus of the present invention having the exciting light source, and it comprises the first component analysis step for collecting the analysis components while the exciting light source is turned off and then analyzing the analysis components, and the second component analysis step for collecting the analysis components while the exciting light source is turned on and then analyzing the analysis components. Therefore, the water-soluble and water-insoluble analysis components can be collected, and thus many types of analysis components can be analyzed.

What is claimed is:

1. A gas collection apparatus having a pipe in which sample atmospheric air serving as a measurement target is supplied and passed and absorption liquid adapted to absorb analysis components contained in the sample atmospheric air is supplied and passed along an inner wall of the pipe, characterized in that a photocatalyst thin film layer containing a photocatalyst which is optically excited upon irradiation of light having specific wavelengths thereto to be made super-hydrophilic is formed on an inner wall of said pipe, and said pipe is formed of material which allows the light having specific wavelengths to be transmitted therethrough.

2. The gas collection apparatus as claimed in claim 1, wherein the light having the specific wavelengths is ultraviolet rays which are contained in light emitted from a white light source or solar light, and the photocatalyst is formed of a material from which the same components as the analysis components or components interfering with analysis of the analysis components are eluted into said absorption liquid at such a small amount that elution of these components has no effect on an analysis precision of the analysis components.

3. The gas collection apparatus as claimed in claim 1, wherein the photocatalyst is formed of anatase type titanium oxide or rutile type titanium oxide.

4. The gas collection apparatus as claimed in claim 1, wherein the photocatalyst thin film layer is designed to be transparent and to have a thickness of 0.01 $\mu$m to 5 $\mu$m.

5. The gas collection apparatus as claimed in claim 1, wherein the photocatalyst thin film layer is designed to be porous.

6. The gas collection apparatus as claimed in claim 1, wherein said pipe is designed so that a light attenuation coefficient of said pipe at the specific wavelengths is equal to 90% or less.

7. The gas collection apparatus as claimed in claim 6, wherein said pipe is designed so that a light attenuation coefficient of said pipe at the specific wavelengths is equal to 50% or less.

8. The gas collection apparatus as claimed in claim 1, further including a cooling apparatus for cooling a part or the overall of the inside of said pipe.

9. The gas collection apparatus as claimed in claim 8, wherein cooling temperature of a part or the overall of the inside of said pipe by said cooling apparatus is set in a range of 0° C. to 10° C.

10. A gas analysis apparatus including said gas collection apparatus as claimed in claim 1, and a component detection apparatus to which the absorption liquid is fed along said inner wall of said pipe to detect analysis components contained in the absorption liquid, said gas collection apparatus being disposed in an environment exposed to irradiation of light from one of a white light source and the sun, said one of a white light source and the sun both having specific wavelengths adapted to optically excite said photocatalyst of said photocatalyst thin film layer formed on said inner wall of said pipe, and photocatalyst and said photocatalyst thin film layer thereby being rendered super-hydrophilic.

11. The gas analysis apparatus as claimed in claim 10, wherein said component detection apparatus comprises concentrating means for concentrating analysis components contained in the absorption liquid, desorption means for desorbing from said concentrating means the analysis components concentrated by said concentrating means, and component detection a means for detecting the analysis components which are desorbed from said concentrating means.

12. The gas analysis apparatus a claimed in claim 11, wherein said concentrating means of said component detection apparatus comprises a concentrating column which is filled with adsorbent for adsorbing the analysis components contained in the absorption liquid.

13. The gas analysis apparatus as claimed in claim 11, wherein the absorption liquid from which the analysis components are removed when it is passed through the concentrating means is circulatively fed to the gas collection apparatus.

14. The gas analysis apparatus as claimed in claim 10, wherein said component detection apparatus comprises one of a liquid chromatograph and an ion chromatograph.

15. The gas analysis apparatus as claimed in claim 10, further including an exciting light source for one of continuously and intermittently irradiating said pipe with light having the specific wavelengths to optically excite said photocatalyst contained in said photocatalyst thin film layer formed on said inner wall of said pipe of said gas collection apparatus.

16. A gas analysis method using said gas analysis apparatus as claimed in claim 15, comprising:

a first component analyzing step of collecting the analysis components serving as analysis targets from the sample atmospheric air serving as a measurement target by the gas collection apparatus in a state where the exciting light source is turned off, and then analyzing the analysis components thus collected by the component detection apparatus; and a second component analysis step of collecting the analysis components serving as analysis targets from the sample atmospheric air serving as a measurement target by the gas collecting apparatus in a state where the exciting light source is turned on, and then analyzing the analysis components thus collected by the component detection apparatus.

* * * * *